US009562854B2

(12) United States Patent
Sherif et al.

(10) Patent No.: US 9,562,854 B2
(45) Date of Patent: Feb. 7, 2017

(54) MODIFYING THE SPATIAL DISTRIBUTION OF THE REFRACTIVE INDEX OF AN OBJECT AND IMAGING THE OBJECT USING INTERFEROMETRY

(75) Inventors: Sherif S. Sherif, Winnipeg (CA); Pedro Fernando Pereira Bogado, Winnipeg (CA)

(73) Assignee: UNIVERSITY OF MANITOBA, Winnipeg (CA)

(*) Notice: Subject to any disclaimer, the term of this patent is extended or adjusted under 35 U.S.C. 154(b) by 141 days.

(21) Appl. No.: 13/640,200

(22) PCT Filed: Apr. 13, 2011

(86) PCT No.: PCT/CA2011/000422
§ 371 (c)(1),
(2), (4) Date: Dec. 19, 2012

(87) PCT Pub. No.: WO2011/127584
PCT Pub. Date: Oct. 20, 2011

(65) Prior Publication Data
US 2013/0094030 A1    Apr. 18, 2013

Related U.S. Application Data

(60) Provisional application No. 61/323,643, filed on Apr. 13, 2010.

(51) Int. Cl.
G01N 21/45 (2006.01)
G01N 21/47 (2006.01)
(Continued)

(52) U.S. Cl.
CPC .......... *G01N 21/45* (2013.01); *G01B 9/02004* (2013.01); *G01B 9/02029* (2013.01);
(Continued)

(58) Field of Classification Search
CPC ............ G01B 9/02004; G01B 9/02029; G01B 9/02087; G01B 9/02091; G01N 21/1717; G01N 21/45; G01N 21/4795
(Continued)

(56) References Cited

U.S. PATENT DOCUMENTS 6,002,480 A * 12/1999 Izatt et al. ................ 356/479
7,031,054 B2 * 4/2006 Cathey et al. ............ 359/363
(Continued)

OTHER PUBLICATIONS

Chuanyong Huang, Bin Liu, and Mark E. Brezinski, "Ultrasound-enhanced optical coherence tomography: improved penetration and resolution", Apr. 2008, J Opt Soc Am A Opt Image Sci Vis., 25(4): 938-946.*

(Continued)

Primary Examiner — Kara E Geisel
Assistant Examiner — Violeta A Prieto
(74) Attorney, Agent, or Firm — Mueting, Raasch & Gebhardt, P.A.

(57) ABSTRACT

Methods and/or systems are disclosed herein for use in imaging an object including using interferometry while modifying at least one characteristic of the object such as the spatial distribution of the refractive index of the object. The interferometry imaging data may be processed with one or more image processing algorithms that take into account the modification, or change, in the spatial distribution of the refractive index of the object.

36 Claims, 17 Drawing Sheets

(51) Int. Cl.
G01B 9/02 (2006.01)
G01N 21/17 (2006.01)

(52) U.S. Cl.
CPC ..... *G01B 9/02087* (2013.01); *G01B 9/02091* (2013.01); *G01N 21/4795* (2013.01); *G01N 21/1717* (2013.01)

(58) Field of Classification Search
USPC .......................... 356/571, 481, 518, 479, 497
See application file for complete search history.

(56) References Cited

U.S. PATENT DOCUMENTS

| | | | | |
|---|---|---|---|---|
| 7,508,523 B2* | 3/2009 | Chang et al. | ................. | 356/479 |
| 2004/0109164 A1* | 6/2004 | Horii et al. | ................... | 356/479 |
| 2004/0263859 A1* | 12/2004 | Chang et al. | ................. | 356/497 |
| 2005/0088745 A1* | 4/2005 | Cathey et al. | ................. | 359/568 |
| 2006/0109478 A1* | 5/2006 | Tearney et al. | ............... | 356/479 |
| 2007/0183584 A1* | 8/2007 | Baumann et al. | ............ | 378/145 |
| 2008/0198367 A1* | 8/2008 | Chang et al. | ................... | 356/73 |
| 2008/0228073 A1* | 9/2008 | Silverman et al. | ........... | 600/437 |
| 2009/0312628 A1* | 12/2009 | Igarashi | ........................ | 600/425 |

OTHER PUBLICATIONS

Abubakar et al. "Iterative forward and inverse algorithms based on domain integral equations for three-dimensional electrical and magnetic objects". 2004. *Journ. Of Computational Physics.* 195(1):236-262.
Adie et al. "Detection of multiple scattering in optical coherence tomography using the spatial distribution of Stokes vectors". 2007. *Optics Express.* 15(26):18033-18049.
Bouma and Tearney, eds., Handbook of Optical Coherence tomography. (Marcel Dekker, New York, 2001). Title Page, Copyright Page, and Table of Contents. Total of 4 pages.
Cathey et al. "Image gathering and processing for enhanced resolution". 1984. *J. Opt. Soc. Am.* A. 1:241-250.
Cathey et al. "New paradigm for imaging systems". 2002. *Appl. Opt.* 41:6080.
Chi et al. "Electronic imaging using a logarithmic asphere". 2001. *Opt. Lett.* 26:875-877.
Conchello. "Superresolution and convergence properties of the expectation maximization algorithm for maximum-likelihood deconvolution of incoherent images". 1998. *J. Opt. Soc. Am. A.* 15:2609-2619.
Dowski et al. "Extended depth of field through wave-front coding". *Appl. Opt.* 34:1859-1866. 1995.
Eckstein et al. "A practical guide to model observers for visual detection in synthetic and natural noisy images" in Handbook of Medical Imaging. J. Beutel, H. Kundel, R. Van Metter, Eds. (SPIE Press, 2002). Title Page, Copyright Page, Table of Contents, and Chapter 10. 44 pages total.
Fercher et al. "Optical coherence tomography—principles and applications". 2003. *Rep. Prog. Phys.* 66:239-303.
Hopf et al. "Applied Classical Electrodynamics, vol. I: Linear Optics" (CRC Press, Boca Raton, Florida). 2006. Title Page, Copyright Page, and Table of Contents. 6 pages.
Johnson et al. "Passive ranging through wave-front coding: information and application". 2000. *Appl. Opt.* 39:1700-1710.
Kubala et al. "Variable-addressability electronic binocular system". 2002. *Appl. Opt.* 41:707-716.

Mao et al. "Graded-index fiber lens proposed for ultrasmall probes used in biomedical imaging". 2007. *Applied Optics.* 46:5887-5894.
Optical Coherence Tomography. From Wikipedia. 10 pages.
Paxman et al. "Image reconstruction from coded data: II. Code design". 1984. *J. Opt. Soc. Am. A.* 2:501-509.
Schenk et al. "Ultrasound induced improvement in optical coherence tomography (OCT) resolution". 2002. *Proceedings of the National Academy of Sciences.* 99:9761-9764.
Schmitt et al. "Model of optical coherence tomography of heterogeneous tissues". 1997. *Journal of the Optical Society of America A.* 14(6):1231-1242.
Schmitt. "Optical coherence tomography (OCT): a review". 1999. *IEEE Journal of Selected Topics in Quantum Electronics.* 5(4):1205-1215.
Sherif. Depth of Field Control in Incoherent Hybrid Imaging Systems, Ph.D dissertation (University of Colorado, Boulder, Colorado). 2002. Title Page, Description Page and Table of Contents. 11 pages.
Sherif et al. "Reduced depth of field in hybrid imaging systems". 2002. *Appl. Opt.* 41:6062-6074.
Sherif et al. "A Phase plate to extend the depth of field of incoherent hybrid imaging systems". 2004. *Applied Optics.* 43(13):2709-2721.
Sherif et al. "Extended depth of field in hybrid imaging systems: circular aperture". 2004. *Journal of Modern Optics.* 51:1191-1209.
Sherif et al. "Effect of detector noise in incoherent hybrid imaging systems". 2005. *Optics Letters.* 30:2566-2568.
Sherif et al. "Comment on 'extended depth of field in hybrid imaging systems: circular aperture'". 2005. Journal of Modern Optics. 52:1783-1788.
Sherif et al. in Optical Imaging and Microscopy—Techniques and Advanced Systems, $2^{nd}$ Ed., P. Torok and F. Kao Eds. (Springer, Berlin 2007). Ch6, pp. 137-167.
Sherif et al. "Statistics of the depth-scan photocurrent in time-domain optical coherence tomography". 2008. *Journal of the Optical Society of America A.* 25:16-20.
Shung. "Diagnostic Ultrasound: Imaging and Blood Flow Measurements". (CRC Press, Boca Raton, Florida). 2006.
Xu et al. "Spectroscopic spectral-domain optical coherence microscopy" 2006. *Opt. Lett.* 31:1079-1081.
Yadlowsky et al. "Multiple scattering in optical coherence microscopy". 1995. *Appl. Opt.* 34:5699-5707.
Yan et al. "Accelerating reconstruction of reference digital tomosynthesis using graphics hardware". 2007. *Medical Physics.* 34:3768-3776.
Zysk et al. "Computational methods for analysis of human breast tumor tissue in optical coherence tomography images". 2006. *Journal of Biomedical Optics.* 11(5):054015.
International Search Report issued on Jul. 29, 2011 in related PCT application No. PCT/CA2011/000422. 3 pages.
Written Opinion of the International Searching Authority. Issued Jul. 29, 2011 in related application PCT/CA2011/000422. 4 pages.
International Preliminary Report on Patentability. Issued on Oct. 26, 2012, in related application PCT/CA2011/000422. 5 pages.
Brady et al. "Integrated analysis and design of analog and digital processing in Imaging Systems: Introduction to the feature issue". 2002. *Appl. Opt.* 41:6049.
Dowski et al. Single-lens single-image incoherent passive-ranging systems. 1994. *App. Opt.* 33:6762-6773.
Sherif et al. "Maximum likelihood estimation of depth reflectance in time-domain optical coherence tomography" in Optical Coherence Tomography and Coherence Techniques III. P. Ander and Z. Chen, eds., vol. SPIE vol. 6627 of Progress in Biomedical Optics and Imaging (Optical Society of America, 2007). 16 pages total.

* cited by examiner

MODIFYING THE SPATIAL DISTRIBUTION OF THE REFRACTIVE INDEX OF AN OBJECT AND IMAGING THE OBJECT USING INTERFEROMETRY

CROSS-REFERENCE TO RELATED APPLICATION

This application is the §371 U.S. National Stage of International Application No. PCT/CA2011/000422, filed 13 Apr. 2011, which claims the benefit of U.S. Provisional Application Ser. No. 61/323,643 filed 13 Apr. 2010, entitled "IMPROVED OPTICAL COHERENCE TOMOGRAPHY," which are incorporated herein by reference in their entireties.

BACKGROUND

The present disclosure relates generally to imaging using interferometry. More particularly, the present disclosure pertains to the use of methods and systems using optical coherence tomography (OCT) for various biological tissue imaging applications including, e.g., tumor detection (e.g., early detection), dental caries detection (e.g., early detection), wounds and/or burnt tissue imaging, etc. Further, such methods and systems using optical coherence tomography may be useful in the following fields: ophthalmology, surgery, cardiology, neurology, gastroenterology, and/or dermatology.

OCT has established itself as an important imaging modality for numerous medical and biological applications. Generally, OCT is a sub-surface imaging technique that uses either a low-coherence light source (time-domain systems) or a swept source (frequency-domain systems). OCT has about one to about two orders of magnitude higher resolution than ultrasound imaging and an imaging depth of about 4 to about 6 millimeters. Further, OCT may be implemented using an optical fiber based probe that is mounted on a syringe to image internal body organs (see, e.g., Y. Mao, S. Chang, S. S. Sherif, and C. Flueraru, "Graded-index fiber lens proposed for ultrasmall probes used in biomedical imaging," *Applied Optics*, 46, pp. 5887-5894 (2007)).

The use of light in OCT techniques may be safer to most biological samples than ionizing radiation like X-rays or gamma rays, and further may allow for spectroscopic characterization of an object, e.g., to detect tumor in tissue (see, e.g., Chengyang Xu, Claudio Vinegoni, Tyler S. Ralston, Wei Luo, Wei Tan, and Stephen A. Boppart, "Spectroscopic spectral-domain optical coherence microscopy," *Opt. Lett.* 31, 1079-1081 (2006)).

FIG. 1 depicts the image resolution and penetration depth for different biomedical imaging modalities. As shown, a tradeoff may exist between the imaging resolution and penetration depth in sub-surface biomedical imaging applications. In addition to the relatively low cost of OCT, another advantage may be its combination of imaging resolution and penetration depth that may be unattainable by other biomedical imaging modalities.

Further, the ability of OCT to detect microscopic changes in the morphology and composition of tissue may make OCT an ideal non-invasive optical biopsy method for the early detection of cancer (see, e.g., B. E. Bouma and G. J. Tearney, eds., *Handbook of Optical Coherence Tomography* (Marcel Dekker, New York, 2001)).

Many OCT imaging models only consider single scattered photons (e.g., ballistic photons) inside an object as contributors to the imaging process. While ballistic-photon-based mathematical OCT models may simplify the analysis, it has been demonstrated that multiple-scattered photons, or multiple-scattered light, which are dominant at large depths, may be a fundamental limitation in increasing the imaging depth of OCT in tissue (see, e.g., M. J. Yadlowsky, J. M. Schmitt, and R. F. Bonner, "Multiple scattering in optical coherence microscopy," *Appl. Opt.* 34, 5699-5707 (1995)). Recent application of OCT imaging for the early detection of breast cancer may represent an area where increased imaging depth may be useful (see, e.g., A. M. Zysk and S. A. Boppart, "Computational methods for analysis of human breast tumor tissue in optical coherence tomography images," *Journal of Biomedical Optics* 11 (5), 054015 (2006)).

When an optical field is incident on biological tissue, the optical field penetrates the tissue to a depth that depends on the optical properties of biological tissue and the intensity of the field. Biological tissue is typically an inhomogeneous optical medium, and therefore, part of the optical field is reflected. The light that is scattered once inside the tissue is called the single-scattered photons or light; the light that is scattered more than once inside the tissue is called multiple-scattered photons or light. In other words, light that is only scattered by one localized scattering center is called single-scattered light, and light that is scattered by more than one localized scattering center grouped together is known as multiple scattered light.

In OCT imaging, backscattered light, which is the light reflected back to where it came from, may be used to reconstruct the subsurface structure of an object, even though the detected light has both single and multiple-scattered components. As imaging depth increases, the ratio of detected single to multiple-scattered components decreases. As such, multiple scattering of light introduces a loss of contrast in OCT images, reduces the imaging axial resolution, and decreases the imaging depth in biological tissue (see, e.g., Schmitt, J. M., "Optical coherence tomography (OCT): a review," *IEEE Journal of Selected Topics in Quantum Electronics* 5(4), 1205-1215 (1999); Schmitt, J. M., and Knüttel, A., "Model of optical coherence tomography of heterogeneous tissue," *Journal of the Optical Society of America A* 14(6), 1231-1242 (1997); and Fercher, A. F., Drexler, W., Hitzenberger, C. K., and Lasser, T., "Optical coherence tomography-principles and applications," *Reports on Progress in Physics* 66, 239-303 (2003)).

Several researchers have studied multiple-scattered light in biological tissue to characterize its effects on OCT imaging. For example, Yadlowsky et al. has experimentally classified the directions of multiply scattered light into small and wide angles (see, e.g., Yadlowsky, M. J., Schmitt, J. M., and Bonner, R. F., "Multiple scattering in optical coherence microscopy," *Applied Optics* 34(25), 5699-5707 (1995)). It was demonstrated that multiple-scattered light with small angles may contribute to backscattered light and may enhance the reflectance of small structures of biological tissue. Further, it was also demonstrated that multiple-scattered light with wide angles may reduce the contrast of subsequent features, and blurred and produced broad haze in OCT images.

Further, for example, Adie et al. quantified multiple-scattering of light using a polarization sensitive OCT system (see, e.g., Adie, S. G., Hillman, T R., and Sampson, D. O., "Detection of multiple scattering in optical coherence tomography using the spatial distribution of Stokes vectors," *Optics Express* 15(26), 18033-18049 (2007)). It was demonstrated that the correlation of both local polarization states of the backscattered light may characterize the relative presence of both the multiple-scattered and the single-scattered light from biological tissue.

Each of the methods presented by Yadowlsky et al. and Adie et al. are empirical in nature and were performed for specific biological tissue types using time-domain optical coherence tomography rather than swept-source optical coherence tomography.

Further, an ad-hoc attempt to perform time-domain OCT in the presence of continuous-wave (CW) ultrasound in tissue has been previously discussed (see, e.g., J. O. Schenk and M. E. Brezinski, "Ultrasound induced improvement in optical coherence tomography (OCT) resolution," *Proceedings of the National Academy of Sciences*, 99, pp. 9761-9764 (2002)). In this ad-hoc attempt, a 7.5-MHz ultrasound transducer was placed approximately in parallel to the OCT beam, and the ultrasound beam was brought into direct contact with the tissue with ultrasound transducing medium. The OCT imaging was performed with the ultrasound beam in three settings: ultrasound off, pulsed ultrasound, and CW ultrasound. The CW ultrasound was performed at a power of 10.6 milliwatts (mW), beam diameter of 0.15 centimeters (cm), and focal length of 2.1 cm. The pulsed ultrasound was performed with an average power of 17.8 mW, beam diameter of 0.24 cm, and a focal length of 2.1 cm. Further, the ultrasound beam was used over 1.5 cm proximal to the focus, resulting in an essentially collimated beam, and the pulse repetition rate was 1.3 milliseconds (ms) with an average pulse intensity of 225 Watts per cm squared.

As reported in this article (i.e., "Ultrasound induced improvement in optical coherence tomography (OCT) resolution"), the presence and absence of a CW ultrasound beam is apparent. More specifically, it can be seen that the noise between scatterers may be reduced in the presence of ultrasound deep within the tissue. The article generally concluded that combining OCT with a parallel ultrasound beam may result in an improvement in resolution through a reduced effect of multiple scattering due to photon-phonon interaction. The techniques described in the article, however, only utilized Time-Domain OCT, and further, the OCT algorithms did not take into consideration, or account for, the effects of the CW ultrasound within the tissue in the processing of imaging data and/or constructing of an image from such imaging data.

An integrated computational imaging system (also referred to as a hybrid imaging system) combines a modified optical imaging system and a digital post-processing step. An integrated computational imaging system is different from a system obtained by cascading a physical imaging system and a digital image processing step. In an integrated computational system, both the physical imaging and digital modules are parts of a single system and the imaging process is divided between them. Thus, in an integrated computational system, the final image is obtained by digitally processing an intermediate detected image. The design flexibility of an integrated computational system could be used to achieve imaging performance that would be otherwise unattainable by any similar conventional system (see, e.g., W. T. Cathey and E. R. Dowski, "New paradigm for imaging systems," *Appl. Opt.*, 41, pp. 6080 (2002)).

One example of an integrated computational imaging system may be described in U.S. Pat. No. 7,031,054 B2 entitled "Methods and Systems for Reducing Depth of Field of Hybrid Imaging Systems" issued on Apr. 18, 2006 to Cathey, Jr. et al., which is hereby incorporated herein by reference.

SUMMARY

The disclosure herein relates to methods and systems for use in imaging an object using interferometry. The refractive index of an object can be described as being spatially distributed inside the volume of an object. In other words, an object can be said to have a spatially-distributed refractive index. The refractive index at any location in an object may be different based on characteristics of that location. For example, the density at a location of an object may change or affect its refractive index. As such, for example, a volume of an object comprised of homogeneous material may have the same refractive index across the entire volume. Conversely, for example, a volume of an object comprised of inhomogeneous material may have different refractive indices across the volume.

Generally, the methods and systems described herein modify the spatial distribution of the refractive index of an object while the object is being imaged using interferometry. The modification of the spatial distribution of the refractive index of the object may reduce the multiple-scattered light during imaging. Further, the methods and systems may process the imaging data collected during imaging in view of, based in part on, or taking into consideration, the modification to the refractive index of the object to generate an image of the object. For example, the modification to the refractive index of the object may be removed, or subtracted, from the imaging data. Further, for example, the modification to the refractive index of the object may be taken into consideration and used during the processing (e.g., linear inversion or non-linear inversion) of the imaging data (e.g., the modification may be taken into consideration and used in the inversion algorithm itself) to obtain an image (e.g., a final image).

One exemplary method for use in imaging an object (e.g., an object where the object's refractive index is spatially distributed) includes modifying the spatial distribution of the refractive index of the object and imaging the object using interferometry (e.g., using optical coherence tomography) as the spatial distribution of the refractive index of the object is being modified to provide imaging data. The exemplary method further includes processing the imaging data based in part on the modification to the spatial distribution of refractive index of the object and constructing an image of the object based on the processed imaging data.

In one or more exemplary methods described herein, modifying the spatial distribution of the refractive index of the object may include delivering ultrasound to the object to modify the spatial distribution of the refractive index of the object to reduce multiple-scattered light. Further, delivering ultrasound to the object to modify the spatial distribution of the refractive index of the object may include delivering ultrasound to the object at one or more selected parameters to impose a selected change in the spatial distribution of the refractive index of the object (e.g., delivering ultrasound to the object at one or more selected parameters may include delivering a first 1 megahertz, 2 megapascal ultrasound beam at 22.5 degrees from normal to the object and a second 1 megahertz, 2 megapascal ultrasound beam at negative 22.5 degrees from normal to the object to impose a standing wave in the spatial distribution of the refractive index of the object). Still further, delivering ultrasound to the object to modify the spatial distribution of the refractive index of the object may include delivering continuous wave ultrasound to the object.

Further, in one or more exemplary methods described herein, modifying the spatial distribution of the refractive index of the object may include modifying a spatial distribution of pressure, density, temperature, etc. of the object.

Still further, in one or more exemplary methods described herein, processing the imaging data based in part on the modification to the spatial distribution of refractive index of the object may include removing the effects of the modification to the spatial distribution of the refractive index of the object from the imaging data and/or inverting the imaging data based in part on the modification to the spatial distribution of the refractive index of the object.

One exemplary system for use in imaging an object (e.g., an object where the object's refractive index is spatially distributed) includes modification apparatus, interferometry apparatus (e.g., optical coherence tomography apparatus), and processing apparatus. The modification apparatus may be configured to modify the spatial distribution of the refractive index of an object. The interferometry apparatus may be configured to image the object to provide imaging data as the spatial distribution of the refractive index of the object is being modified using the modification apparatus. The processing apparatus may be configured to receive the imaging data from the interferometry apparatus. The processing apparatus may be further configured to process the imaging data based in part on the modification to the spatial distribution of the refractive index of the object and to construct an image of the object based on the processed imaging data.

In one or more exemplary systems described herein, the modification apparatus may include ultrasound apparatus configured to deliver ultrasound to the object to modify the spatial distribution of the refractive index of the object to reduce multiple-scattered light. Further, the ultrasound apparatus may be further configured to deliver ultrasound to the object at one or more selected parameters to impose a selected change in the spatial distribution of the refractive index of the object (e.g., a first 1 megahertz, 2 megapascal ultrasound beam at 22.5 degrees from normal to the object and a second 1 megahertz, 2 megapascal ultrasound beam at negative 22.5 degrees from normal to the object to impose a standing wave in the spatial distribution of the refractive index of the object). Still further, the ultrasound apparatus may be further configured to deliver continuous wave ultrasound to the object.

Further, in one or more exemplary systems described herein, the modification apparatus is further configured to modify a spatial distribution of pressure, density, temperature, etc. of the object.

Still further, in one or more exemplary systems described herein, the processing apparatus is further configured to process the imaging data based in part on the modification to the spatial distribution of refractive index of the object by removing effects of the modification to the spatial distribution of the refractive index of the object from the imaging data and/or to process the imaging data based in part on the modification to the spatial distribution of refractive index of the object by inverting the imaging data based in part on the modification to the spatial distribution of the refractive index of the object.

In one or more exemplary methods and/or systems, the imaging the object using interferometry may include delivering electromagnetic energy to the object using a swept-source.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
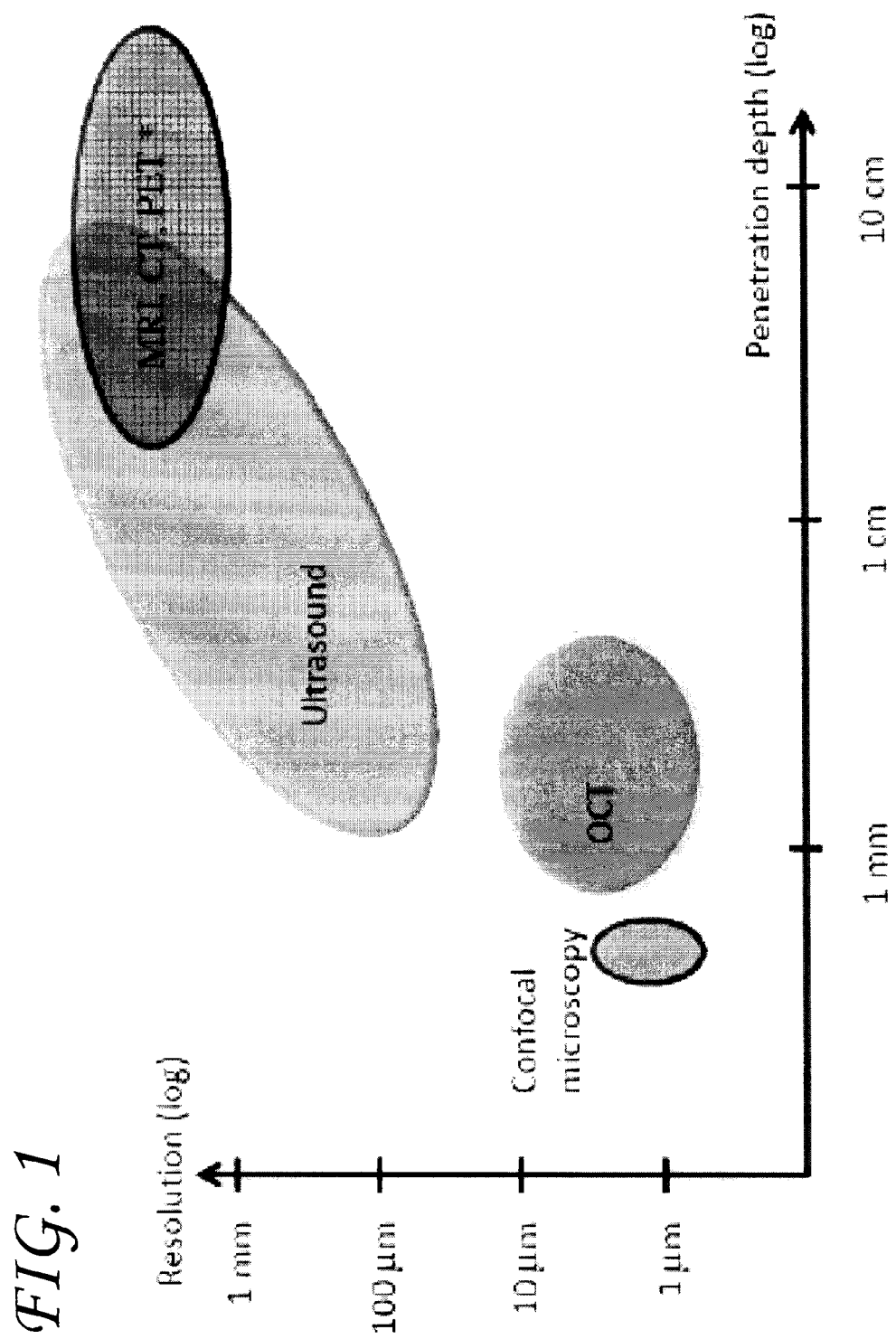
FIG. 1 is a chart displaying image resolution versus penetration depth for different imaging modalities.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, apparatus, and systems shall be described with reference to FIGS. 1-8. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

In the following detailed description of the embodiments, reference is made to drawings which form a part hereof, and in which are shown by way of illustration specific embodiments that may be practiced. It is to be understood that other embodiments may be utilized and processing step/structural changes may be made without departing from the scope of the present disclosure.

The disclosure herein generally describes simultaneously modifying the spatial distribution of an object's refractive index (e.g., by modifying one or more characteristics of the object such as optical characteristics, magnetic characteristics, structural characteristics, etc.) and imaging the object with interferometry (e.g., optical coherence tomography).

For example, one embodiment may include the simultaneous use of ultrasound (as the modification process) and swept-source OCT (as the imaging process) to reduce the negative impact of multiple-scattered light on the penetration depth of swept-source OCT. Further, the use of ultrasound with swept-source OCT systems may be advantageous over the use of ultrasound with time-domain OCT because, e.g., swept-source OCT may have a higher imaging speed and signal-to-noise ratio, swept-source OCT may be used more often than time-domain OCT, and the negative impact of multiple light scattering in tissue may be more serious in swept-source OCT than in time-domain OCT imaging. Although the disclosure herein focuses on the simultaneous use of ultrasound as the modification process and swept-source OCT as the imaging process, ultrasound as well as the other modifications processes may also be used simultaneously with time-domain OCT as well as any other imaging process.

The presence of an ultrasound wave during OCT imaging may introduce a preferred direction for the propagation of light in tissue, thereby reducing the effect of multiply scattered light from 3-D volume (see, e.g., K. K. Shung, "Diagnostic Ultrasound: Imaging and Blood Flow Measurements" (CRC Press, Bocs Raton, Fla., 2006); and F. A. Hopf and G. I. Stegeman, "Applied Classical Electrodynamics, Volume I: Linear Optics" (CRC Press, Bocs Raton, Fla., 2006)).

In swept-source OCT imaging, an inverse Fourier transform may be used to construct an image. However, the effect of modifying, or modulating, tissue with ultrasound may use more processing (e.g., of the interferometric data to extract the image therefrom) to construct the image.

Figure 2:
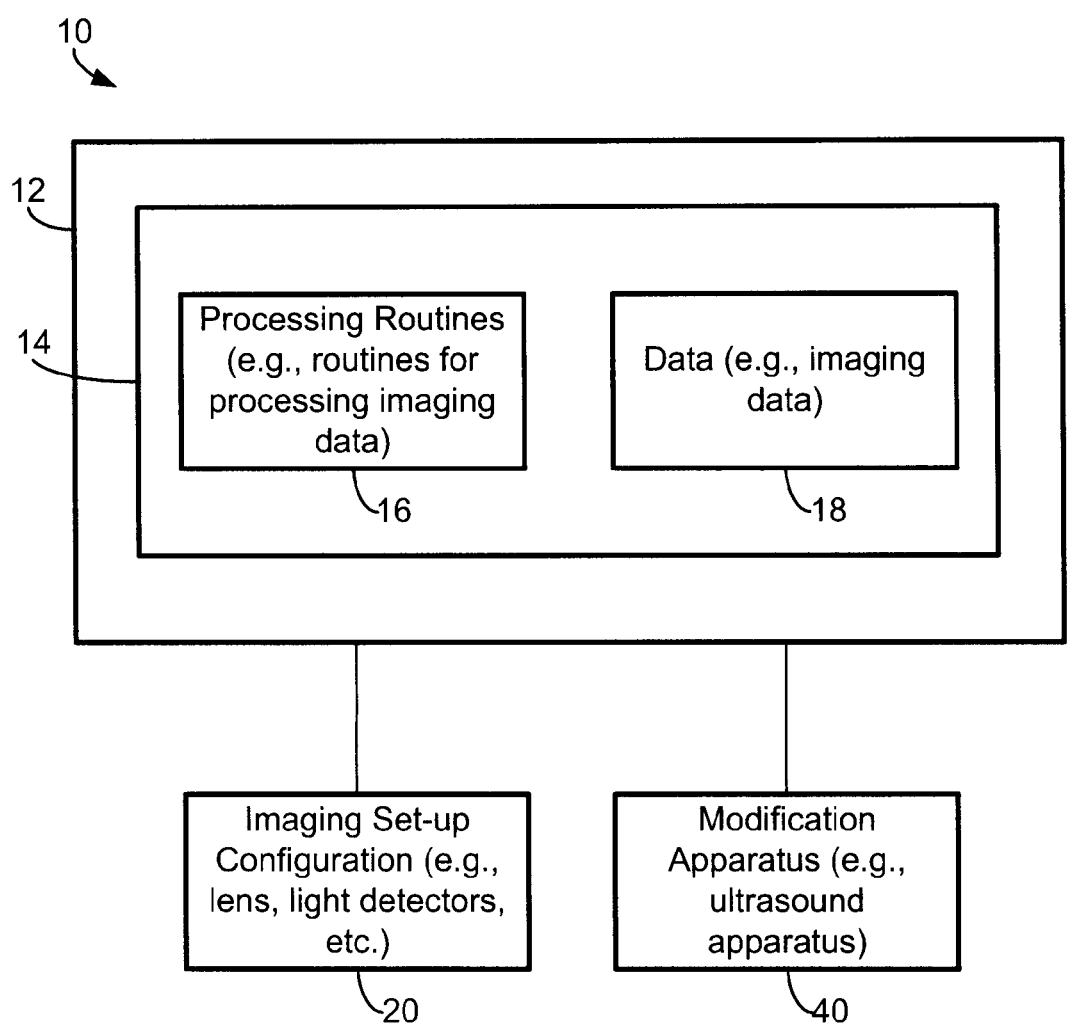
FIG. 2 is a block diagram depicting an exemplary imaging system.

An imaging system 10 to be used in the imaging an object including a processing apparatus (block 12) and data storage (block 14) is depicted in FIG. 2. Data storage (block 14) allows for access to processing programs or routines (block 16) and one or more other types of data (block 18) that may be employed to carry out the illustrative imaging methods, e.g., method 200 as shown generally in the block diagram of FIG. 4.

Exemplary imaging system 10 includes imaging set-up configuration 20 (e.g., controllable or selectable components, such as interferometry components described in U.S. Pat. No. 7,508,523 to Chang et al. or any other interferometry based system used to provide imaging data) and modification apparatus 40.

Figure 3:
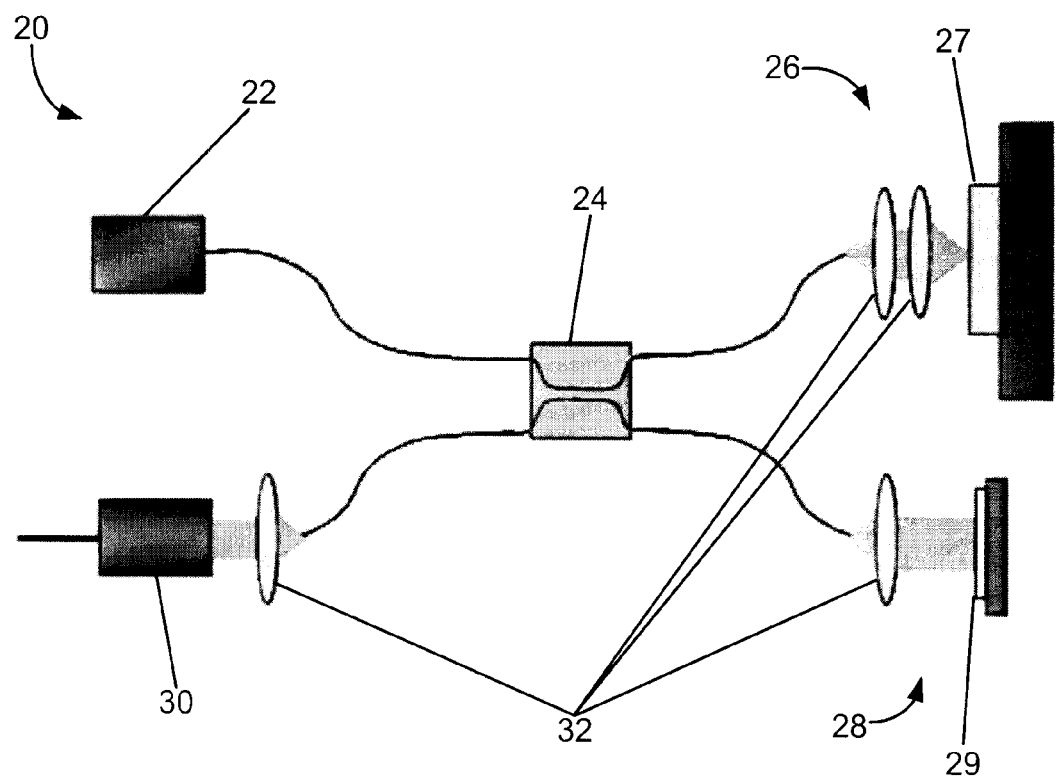
FIG. 3 is a diagram further depicting the imaging set-up of the exemplary imaging system of FIG. 2.

For example, as further described herein with reference to FIG. 3, the image set-up configuration 20 may be any suitable configuration, and further may use any suitable components, to provide the desired imaging functionality described herein (e.g., one or more lenses, one or more light detectors (e.g., photodiodes, charged coupled devices, etc.), radiating sources such as light transmitters, one or more mirrors, couplers, beam-splitters, components of sample or reference arms of interferometry systems, etc.).

Generally, the modification apparatus 40 may be any suitable apparatus capable of modifying one or more characteristics of the object such that at least one optical property of the object to be imaged is modified. More specifically, the modification apparatus 40 (or modulation apparatus) may include any one or more devices and/or systems that are operable to modify (or modulate) an object's refractive index (e.g., the distribution of the object's refractive index).

The modification apparatus 40 may modify an objective's refractive index by modifying one or more optical characteristics, magnetic characteristics, structural characteristics, etc. of the object to be imaged, e.g., by the imaging set-up 20. In at least one embodiment, the modification apparatus 40 may be configured to modify the spatial distribution of pressure within the object, which, in turn, modifies the spatial distribution of the refractive index of the object. In at least another embodiment, the modification apparatus 40 may be configured to modify the spatial distribution of heat within the object, which, in turn, modifies the spatial distribution of the refractive index of the object.

In at least another embodiment, the modification apparatus 40 may include ultrasound apparatus operable to deliver ultrasound to the object. The ultrasound may be delivered at one or more selected parameters (e.g., frequency (e.g., continuous, pulsed, etc.), intensity, pressure, direction, number of beams, number of transducers, number of source directions, etc.) to achieve, generate, or impose a selected, or preferred, modification of the spatial distribution of the object's refractive index. The selected modification of the object's refractive index may be a selected pattern of ultrasound within the object.

Optimal ultrasound wave parameters to minimize multiple scattering may be determined via digital simulations of the interaction of ultrasound with tissue. For example, one may introduce periodic modulation of the simulated tissue's refractive index, along the direction of incidence of the optical OCT beam. This periodic modulation could model the presence of an ultrasound wave. Further, by subsequently examining the effect of different frequencies and intensities of different incident ultrasound waves on the multiply scattered light component, the optimal ultrasound wave parameters to minimize multiple scattering may be determined.

In other words, exemplary ultrasound apparatus may be used to deliver ultrasound to the object to modify the spatial distribution of the object's refractive index, which may, e.g., decrease the amount of multiply scattered light in the object during imaging. To modify the spatial distribution of the object's refractive index, the exemplary ultrasound apparatus may deliver to the object continuous wave ultrasound, pulsed-wave ultrasound, standing-wave ultrasound, e.g., at a selected frequency of about 1 kilohertz to about 5 megahertz (e.g., 1 megahertz).

Exemplary depictions of a simulated homogeneous object being modified with various ultrasound waves of arbitrary amplitudes are shown in FIGS. 5A-5H (e.g., the various ultrasound waves may modify the simulated object's refractive index). The x-axis represents width of the slice or cross-section of the simulated homogeneous object and the y-axis represents depth into the simulated homogeneous object.

Figure 5A:
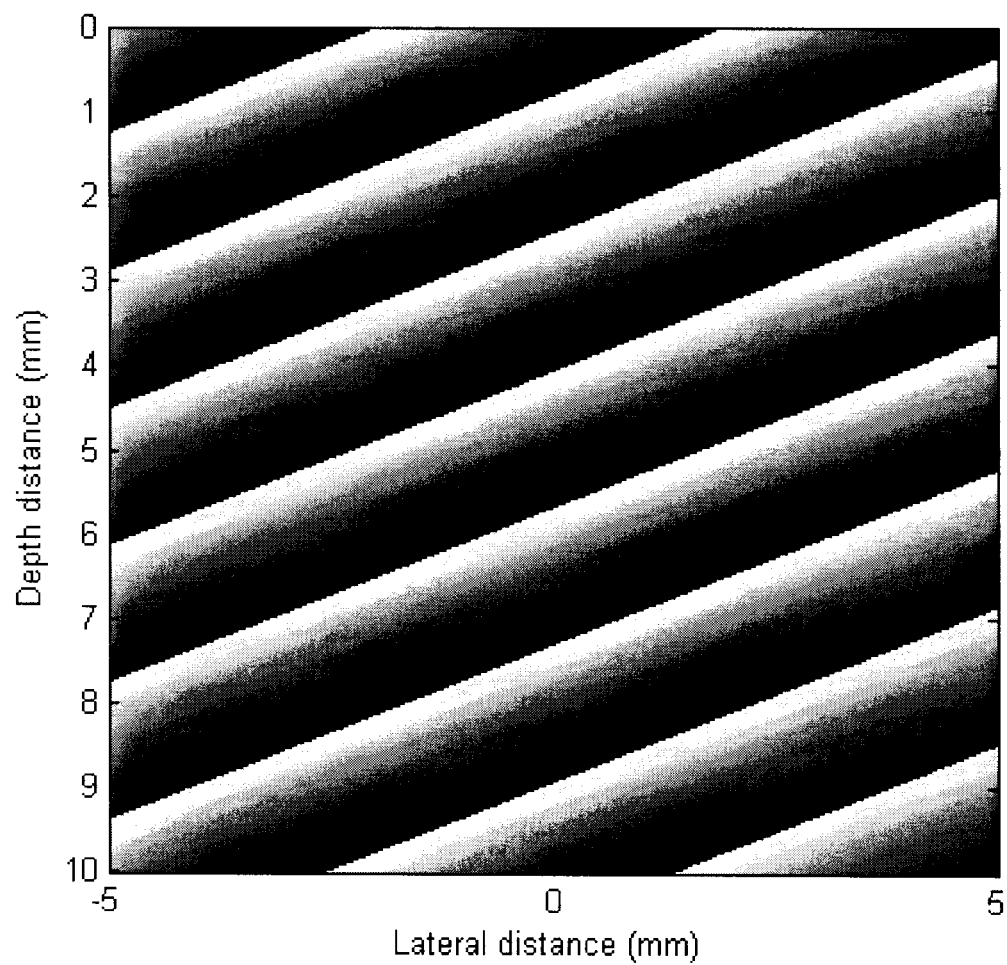
FIGS. 5A-5H are exemplary depictions of a simulated homogeneous object being modified with various ultrasound waves, e.g., delivered by the modification apparatus of the exemplary system of FIG. 2.
Figure 5B:
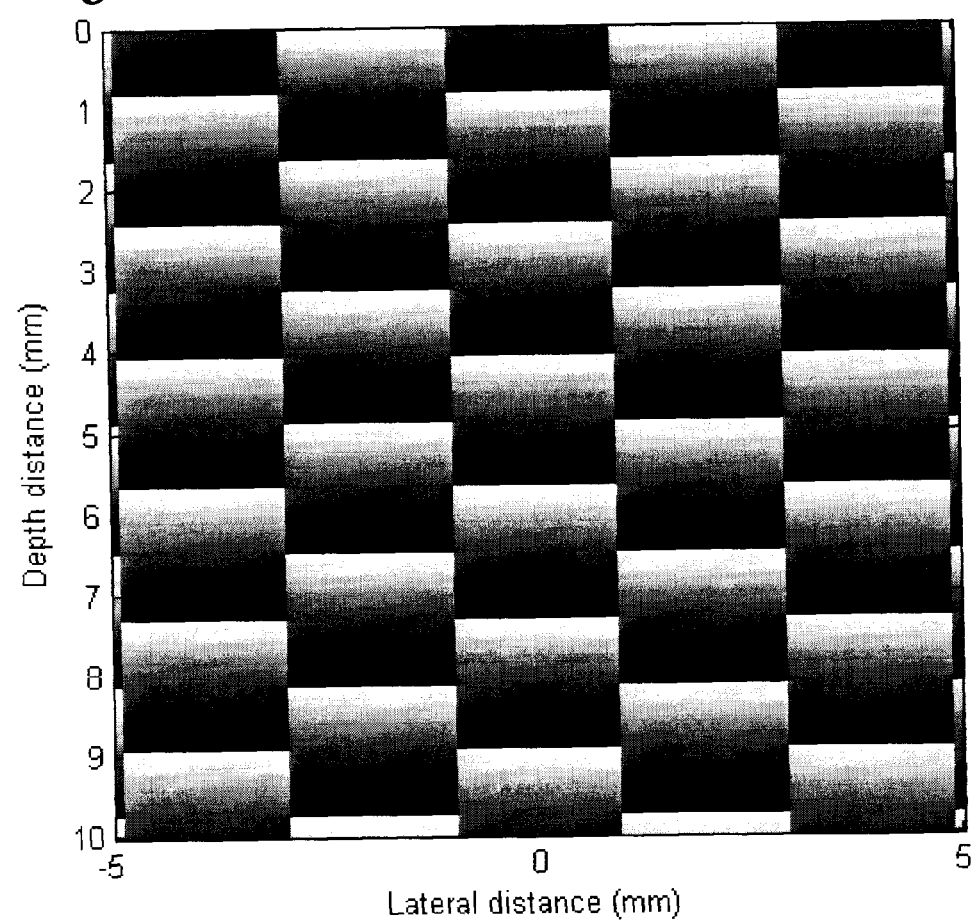
Figure 5C:
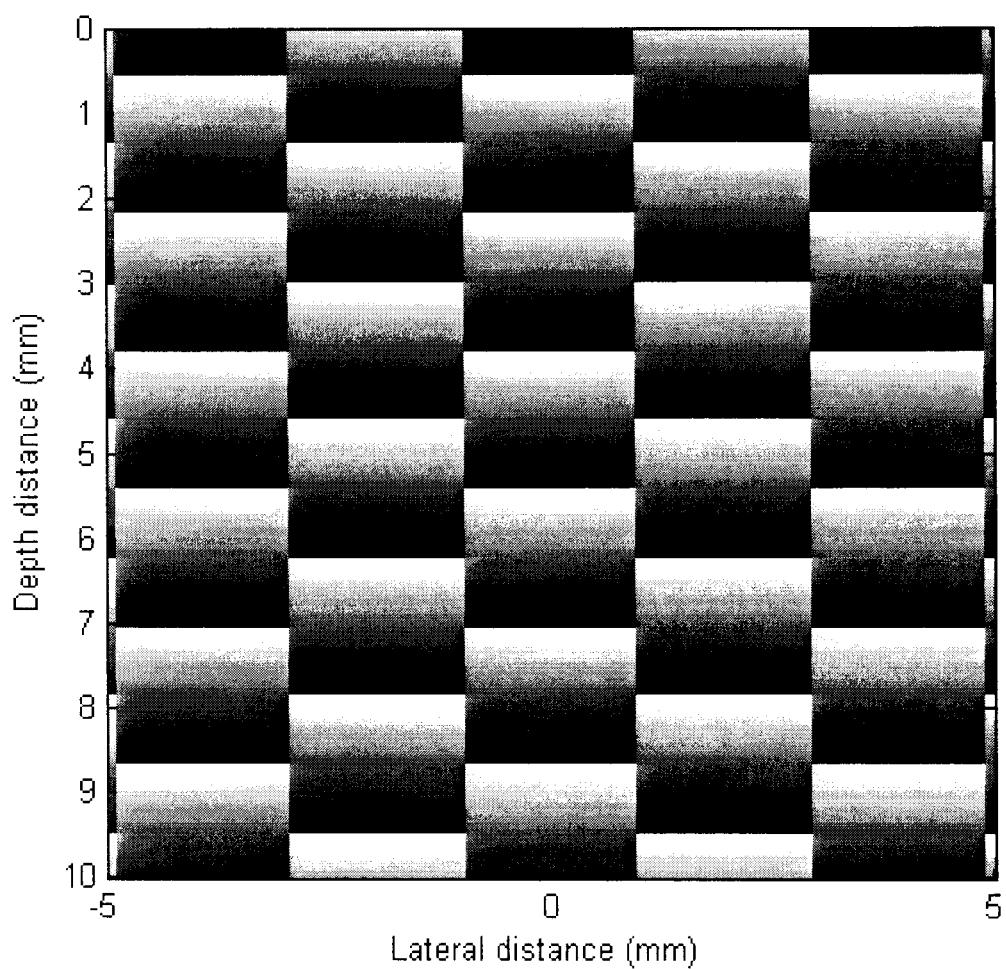
Figure 5D:
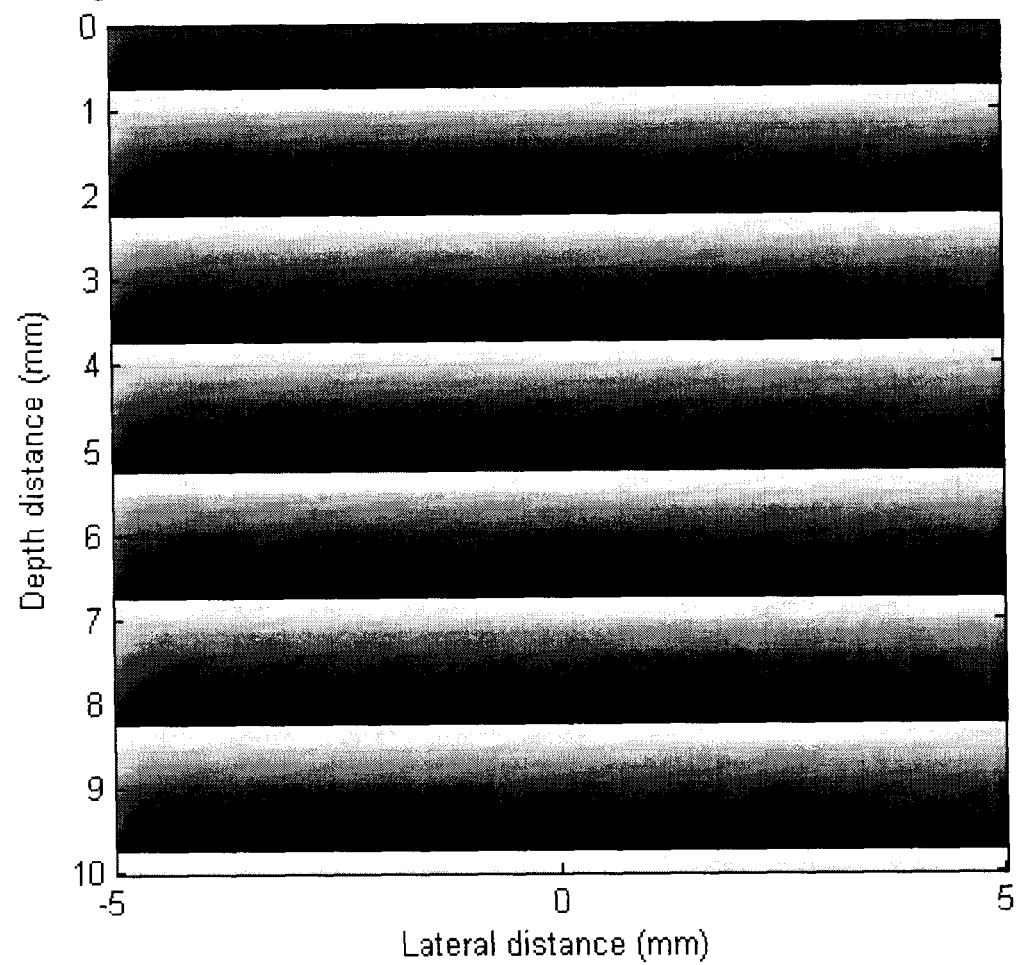
Figure 5E:
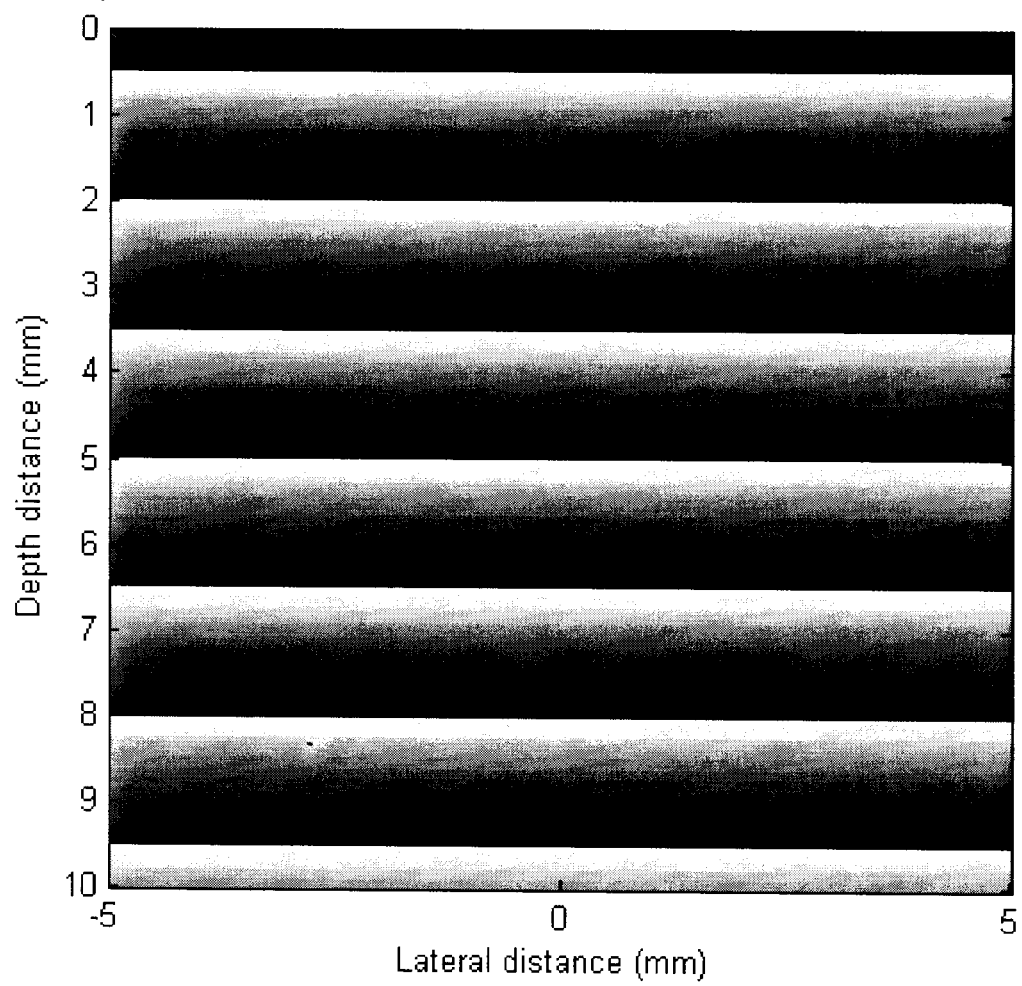
Figure 5F:
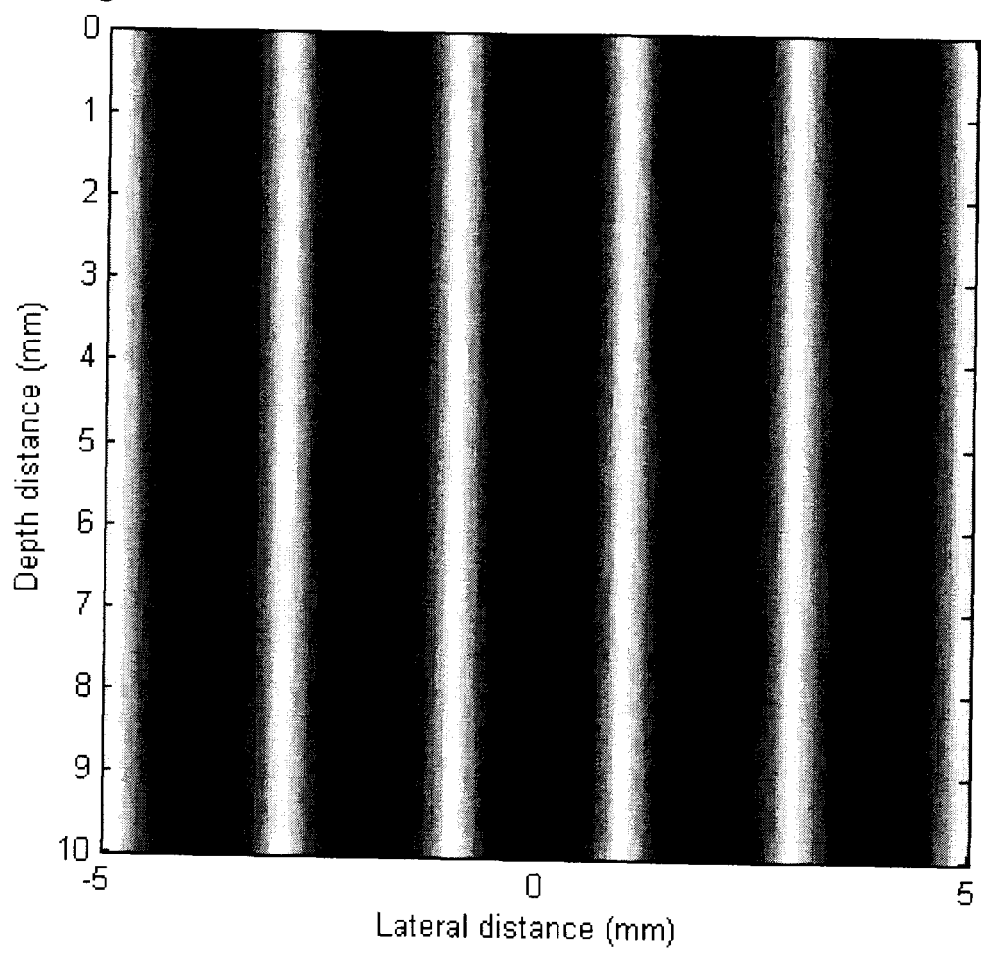
Figure 5G:
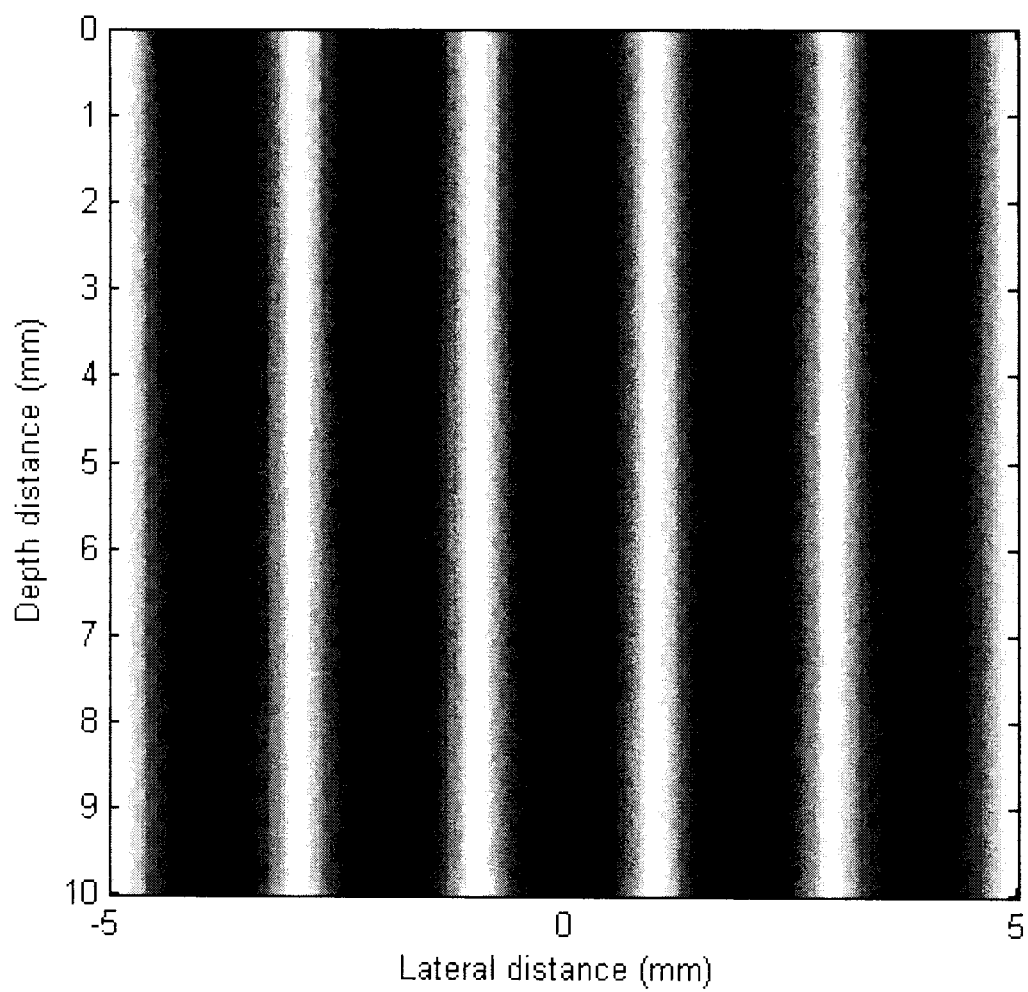
Figure 5H:
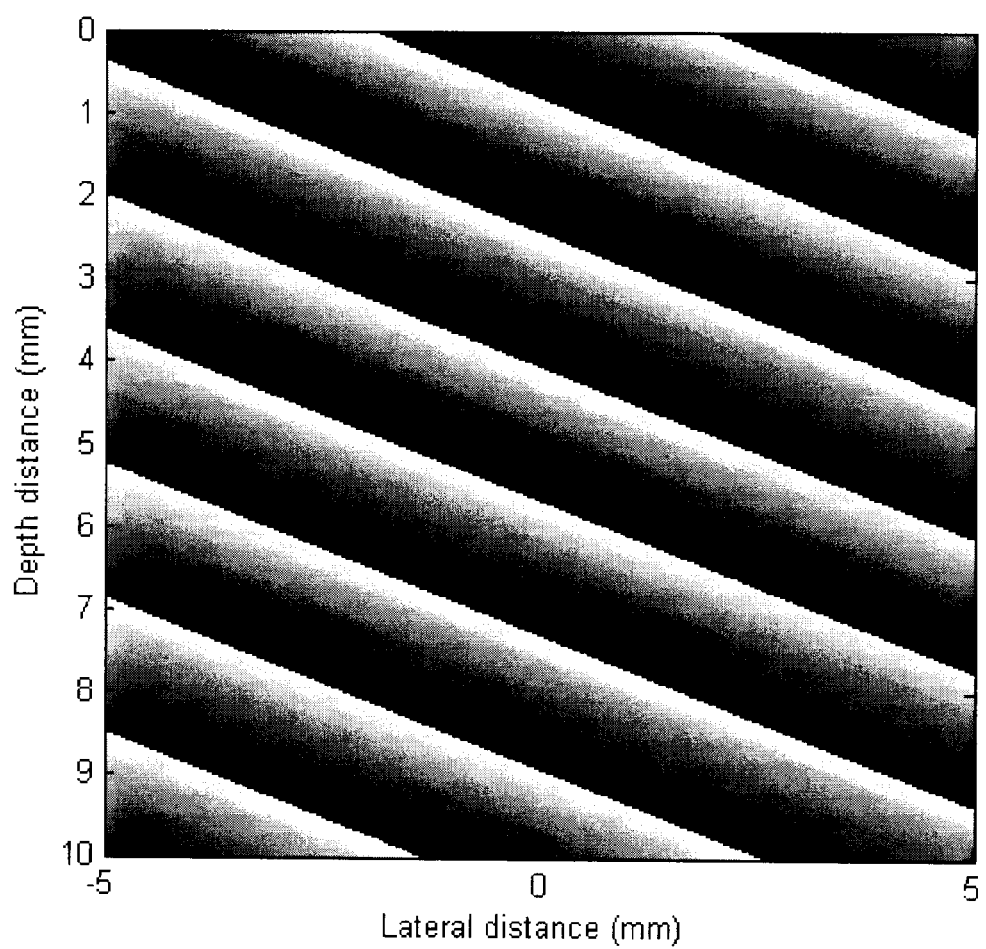

For example, the simulated homogeneous object is being modified with a 1 megahertz inclined (pi/8 radians or 22.5 degrees) plane ultrasound wave in FIGS. 5A & 5H. Further, for example, the simulated homogeneous object is being modified with a 1 megahertz standing ultrasound wave in FIG. 5B (phase) and FIG. 5F (amplitude) at $t_0$ (e.g., a first time instance) and in FIG. 5C (phase) and FIG. 5G (amplitude) at $t_1$ (e.g., a second time instance which follows $t_0$). Still further, for example, the simulated homogeneous object is being modified with a 1 megahertz plane ultrasound wave in FIG. 5D at $t_0$ and in FIG. 5E at $t_1$.

Further, for example, the modification apparatus 40 may include heating apparatus operable to deliver heat to an object, pressure apparatus operable to apply pressure to (or relieve pressure on) an object, electromagnetic apparatus to deliver electromagnetic energy (e.g., magnetic fields) to an object, etc. Pressure, heat, electromagnetic energy, etc. applied to an object to be imaged, may result in modification to the spatial distribution of the object's refractive index.

The modification apparatus 40 and the imaging set-up configuration 20 may further be operably coupled (e.g., fixedly coupled) to each other such that the relationship between the modification being applied to an object (e.g., delivery of ultrasound) and the imaging (e.g., using OCT) is known. For example, the modification apparatus 40 may modify the object in a plane normal to the imaging plane (e.g., the cross-section being imaged), and as such, the spatial relationship between the modification apparatus 40 and the imaging set-up configuration 20 may be configured to achieve such modification. Further, for example, the modification apparatus 40 may modify the object using two beams, one 22.5 degrees from normal to the imaging plane and the other −22.5 degrees from normal to the imaging plane), and as such, the spatial relationship between the modification apparatus 40 and the imaging set-up configuration 20 may be configured to achieve such modification.

In other words, the modification apparatus 40 and the imaging set-up configuration 20 may be configured in a selected spatial relationship. Any one or more structures and/or apparatus may be used to operably couple the modification apparatus 40 and the imaging set-up configuration 20, e.g., to provide the selected spatial relationship, which in turn, may provide a selected change in the spatial distribution of the refractive index of an object.

Exemplary processing programs or routines (block 16) of the imaging system 10 may include programs or routines for performing matrix mathematics, compression algorithms, standardization algorithms, comparison algorithms, vector mathematics, or any other processing required to implement one or more embodiments of the present disclosure as described herein. Further, for example, processing programs or routines (block 16) may include programs or routines for performing "Integrated Computational Imaging," e.g., as described in the following: U.S. Pat. No. 7,031,054 B2 entitled "Methods and Systems for Reducing Depth of Field of Hybrid Imaging Systems" issued on Apr. 18, 2006 to Cathey, Jr. et al.; S. S. Sherif, W. T. Cathey and E. R. Dowski, "A Phase plate to extend the depth of field of incoherent hybrid imaging systems," Applied Optics 43, 2004, pp. 2709; S. S. Sherif, E. R. Dowski, and W. T. Cathey, "Extended depth of field in hybrid imaging systems: Circular aperture," Journal of Modern Optics 51, pp. 1191-1209 (2004); S. S. Sherif, Edward R. Dowski and W. Thomas Cathey, "Effect of detector noise in incoherent hybrid imaging systems," Optics Letters, Vol. 30, pp. 2566-2568 (2005); S. S. Sherif and W. T. Cathey, Optical Imaging and Microscopy Techniques and Advanced Systems, 2nd Ed., P. Torok and F. Kao Eds. (Springer, Berlin, 2007), Ch6, pp. 137-167; S. S. Sherif, Depth of Field Control in Incoherent Hybrid Imaging Systems, Ph.D dissertation (University of Colorado, Boulder, Colo., 2002); and S. S. Sherif and W. T. Cathey, "Reduced depth of field in hybrid imaging systems," Appl. Opt. 41, pp. 6062-6074, 2002, each of which are hereby incorporated herein by reference in their entirety. Such processing programs or routines (block 16) may be used to process imaging data (e.g., acquired using the imaging set-up) in view of the modification to the spatial distribution of the refractive index of the object (e.g., modified by the modification apparatus) and construct an image (e.g., a final image) of an object based on the processed imaging data. In other words, the processing programs or routines (block 16) may be based in part on, or take into consideration, the modified refractive index of object when extracting or constructing a final improved image of the object.

Data (block 18) may include, for example, scattered light/photon data (e.g., interference data, scan data, sampled light/photon data, sampled multiply scattered light data, etc.), data representative of measurements, results from one or more processing programs or routines employed according to the present disclosure, or any other data that may be necessary for carrying out the one or more processes described herein.

In one or more embodiments, the imaging system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or processes as described herein or as would be applied in a known fashion.

The program used to implement the exemplary methods described herein may be provided using any programmable language, e.g., a high level procedural and/or object orientated programming language that is suitable for communicating with a computer system. Any such programs may, for example, be stored on any suitable device, e.g., a storage media, readable by a general or special purpose program, computer or a processor apparatus (e.g., a field programmable gate array) for configuring and operating the computer when the suitable device is read for performing the methods and/or processes described herein. In other words, at least in one embodiment, the imaging system 10 may be implemented using a computer readable storage medium, configured with a computer program, where the storage medium so configured causes the computer to operate in a specific and predefined manner to perform functions described herein.

Likewise, the imaging system 10 may be configured at a remote site (e.g., an application server) that allows access by one or more users via a remote computer apparatus (e.g., via a web browser), and allows a user to employ the functionality according to the present disclosure (e.g., user accesses a graphical user interface associated with one or more programs to process data).

The processing apparatus (block 12), may be, for example, any fixed or mobile computer system (e.g., a personal computer or mini computer). The exact configuration of the computing apparatus is not limiting and essentially any device capable of providing suitable computing capabilities and control capabilities (e.g., control the imaging set up configuration and acquire data, such as interferometry scan data) may be used. Further, various peripheral devices, such as a computer display, mouse, keyboard, memory, printer, scanner, are contemplated to be used in combination with processing apparatus (block 12) of the data storage (block 14).

Further, detectors, sensors, transmitting, and/or receiving components used for collection of data may include any suitable components such as one or more light or image detectors (e.g., charged coupled devices), radiating sources such as light transmitters (e.g., swept-frequency/wavelength laser sources), or any other apparatus used for OCT contemplated to be used in combination with processing apparatus (block 12) of the system 10.

An exemplary imaging set-up configuration 20 is depicted in FIG. 3. The exemplary imaging set-up configuration 20 includes a laser source 22 (e.g., a wavelength/frequency swept-source), a coupler 24 (or beam splitter), a sample arm 26, a reference arm 28, and a detector 30. The sample arm 26 includes the object 27 to be imaged and the reference arm includes a fixed mirror 29. Further, the exemplary imaging set-up configuration 20 includes multiple lenses 32 configured to direct and/or collect electromagnetic energy within the configuration 20 (e.g., at/from the object 27).

Generally, electromagnetic energy may be emitted by the source 22, split by the coupler 24, and directed at each of the sample arm 26 and the reference arm 28 resulting in reflected electromagnetic energy from each of the sample arm 26 and the reference arm 28. The combination (e.g., combined at the coupler 24) of reflected electromagnetic energy (e.g., light) from the sample arm and from the reference arm gives rise to interference patterns. Volume elements of the object 27 that reflect optical energy that may interfere with optical energy from the reference arm, which creates imaging data (e.g., interference patterns) that may be used to construct an image of the object.

Figure 4:
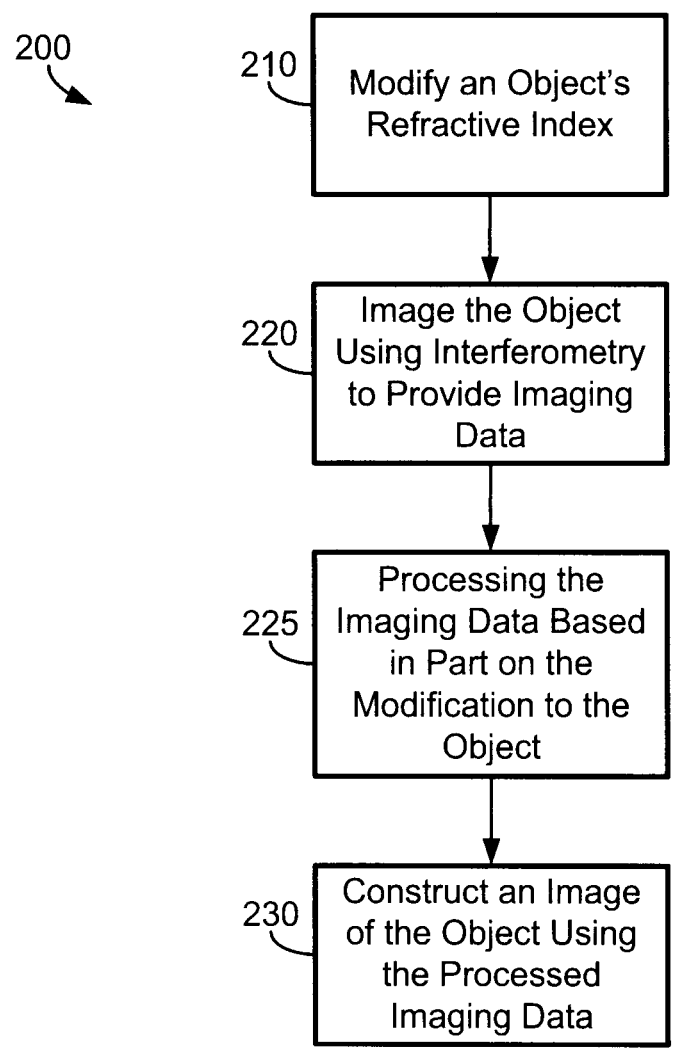
FIG. 4 is a flow chart depicting an exemplary imaging method.

FIG. 4 shows a general block diagram of an illustrative imaging method 200 for imaging an object. One will recognize that one or more of the blocks of functionality described herein may be carried out using one or more programs or routines, and/or any other components of an imaging system, e.g., the imaging system 10 as described herein with reference to FIG. 2.

Generally, the method 200 includes modifying an object's refractive index (e.g., the spatial distribution of the refractive index of the object) (block 210). To modify an object's refractive index, at least one characteristic (e.g., optical characteristics, magnetic characteristics, structural characteristics, etc.) of an object may be modified, e.g., to reduce the detection of multiple-scattered light during imaging.

In one or more embodiments, modifying at least one characteristic of the object includes delivering ultrasound to an object at various selected parameters to change the spatial distribution of the pressure within the object. In other embodiments, modifying at least one characteristic of the object may, e.g., include heating the object, applying pressure to (or relieving pressure on) the object, delivering electromagnetic energy (e.g., magnetic fields) to the object, etc.

The method 200 further includes imaging the object using interferometry (e.g., using imaging set-up configuration 20 described herein with reference to FIG. 3) as the object is being modified to provide imaging data (block 220). In other words, the method 200 may simultaneously modify at least one characteristic of the object to modify the object's refractive index (block 210) and image the object using interferometry to provide imaging data (block 220). As a result, the imaging data may be representative of the object in a modified state (modified by the modification apparatus).

In one or more embodiments, the imaging (block 220) of method 200 is carried out using optical coherence tomography. Further, in one or more embodiments, the imaging (block 220) of method 200 uses a wavelength/frequency swept-source (e.g., the source 22 as depicted in FIG. 3).

The method 200 further includes processing the imaging data (collected in block 220) based in part on the modification to the spatial distribution of the refractive index of the object (block 225) (e.g., using digital image extraction algorithms, using integrated computational imaging systems, etc.) and constructing an image of the object using the processed imaging data (block 230).

Processing the imaging data (block 225) may occur in multiple ways. In at least one embodiment, the imaging data may be processed (e.g., linearly or nonlinearly inverted) (e.g., using known inversion algorithms used in OCT systems), and then the modification to the spatial distribution of the object's refractive index may be removed, or subtracted from the imaging data such that an image of the object may be constructed (block 230).

In at least another embodiment, the inversion algorithm used to invert the imaging data may take into account or consideration the modification to the spatial distribution of the object's refractive index during the processing (e.g., linear or nonlinear inversion) of the imaging data such that an image of the object may be constructed (block 230).

As such, exemplary digital image extraction algorithms may take into account the external modification or modulation of the spatial distribution of the tissue's refractive index due to the presence of the ultrasound wave. In at least one embodiment, linear or nonlinear inversion algorithms may be used in actual swept-source OCT systems. Further, the exemplary digital image extraction algorithms may output an image of the original known object, e.g., the object without the effect of the external modification or modulation of the spatial distribution of the tissue's refractive index due to the presence of an ultrasound wave.

In other words, the illustrative method 200 may include exposing the object to an external stimulus (e.g., ultrasound, heat, pressure, magnetic field, etc.) to modify its material, e.g., optical, magnetic, or structural properties (block 210), which modifies the spatial distribution of the object's refractive index, imaging (e.g., three dimensional subsurface imaging) the modified object using an interferometric technique (e.g., OCT) (block 220), processing the collected imaging data in view of the modification (block 225) (e.g., performing digital signal processing on the acquired data to obtain the 3-D subsurface image of the original object rather than the modified one), and constructing an image based on the processed imaging data (block 230).

Construction of an image (block 230), based on the processed imaging data, may be referred to as an "output" of the method 200. In one or more embodiments, the output (e.g., an image, imaging data, an image data file, a digital file, a file in user-readable format, etc.) of the system and/or methods described herein may be analyzed by a user, used by another machine that provides output based thereon, etc.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by processing apparatus (block 14) described herein.

Also, as described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user.

Generally, the methods and systems as described herein may utilize algorithms implementing matrix mathematics (e.g., matrix inversions, substitutions, etc.), compression algorithms, standardization algorithms, comparison algorithms, vector mathematics, and/or any processing that may be used to construct and/or reconstruct the images described herein (e.g., from sampled multiply scattered light data, etc.).

Figure 6:
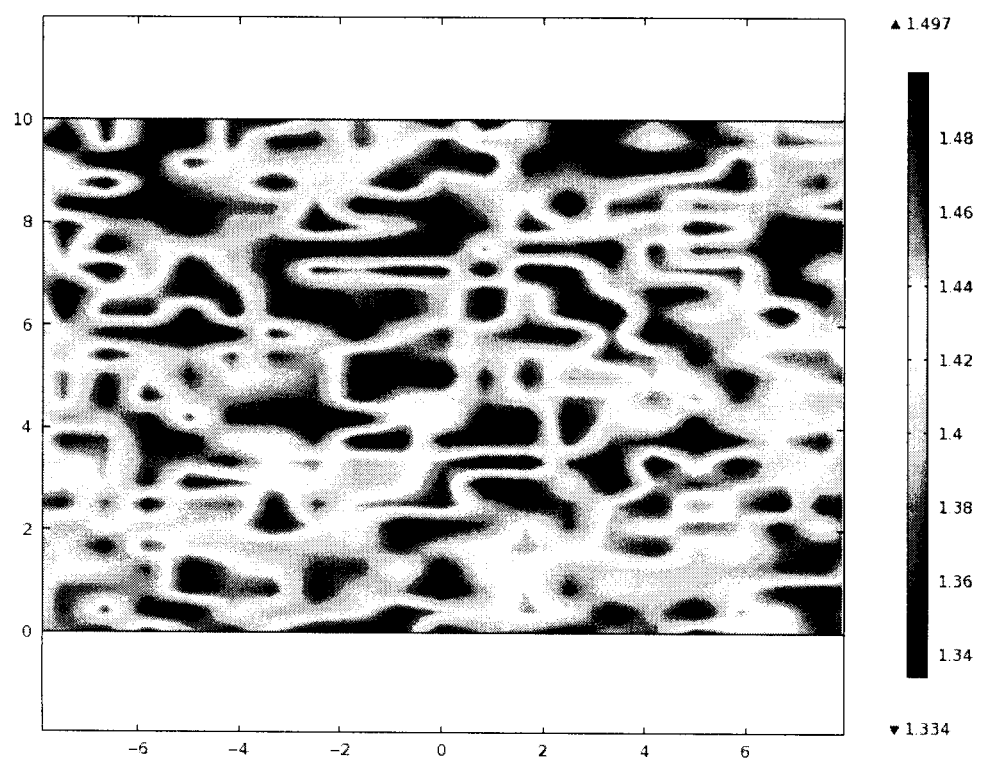
FIG. 6 is an exemplary depiction of a simulated inhomogeneous object (e.g., tissue).

Exemplary depictions of simulated objects are depicted in FIGS. 6-8 and may be used to describe the exemplary systems and methods described herein. The x-axis represents width (e.g., in millimeters) of the slice or cross-section of the simulated objects and the y-xis represents depth (e.g., in millimeters) into the simulated objects. The scale used to depict the index of refraction of the simulated objects is shown in each of FIGS. 6-8 on the right side of the cross-section.

An exemplary depiction of a simulated inhomogeneous object is shown in FIG. 6. As shown, the index of refraction varies within the inhomogeneous object of FIG. 6 from about 1.333 to about 1.500 (which, e.g., may represent a range of the index of refraction for human tissue).

Figure 7A:
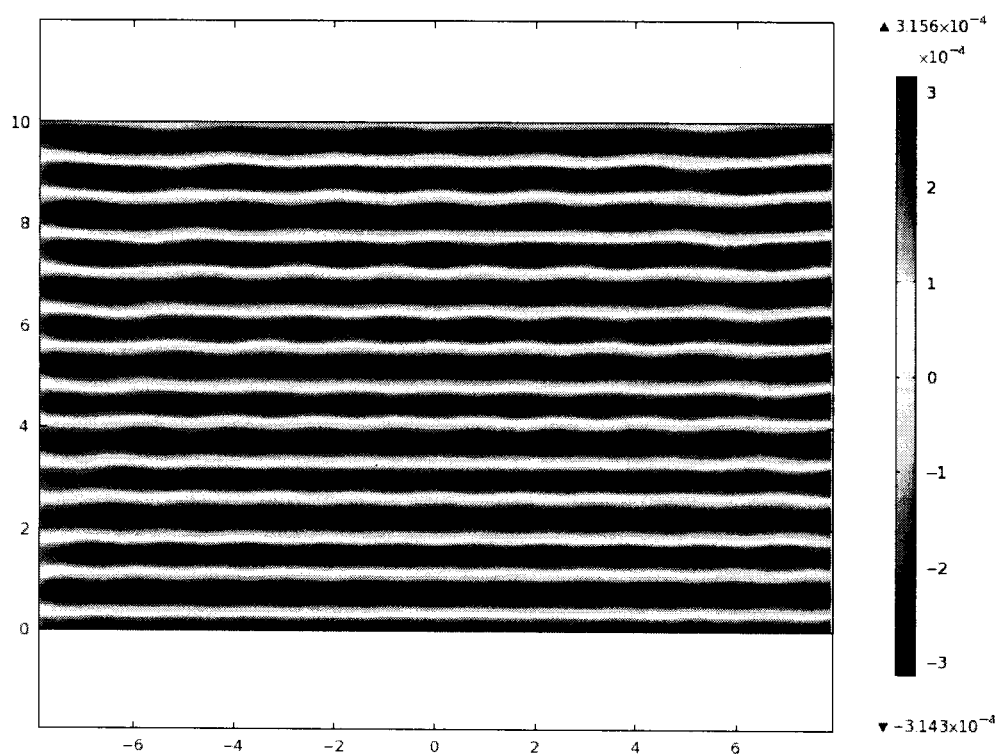
FIG. 7A is an exemplary depiction of a simulated homogeneous object in which the spatial distribution of the refractive index of the simulated homogeneous object is being modified by an ultrasonic plane wave.
Figure 7B:
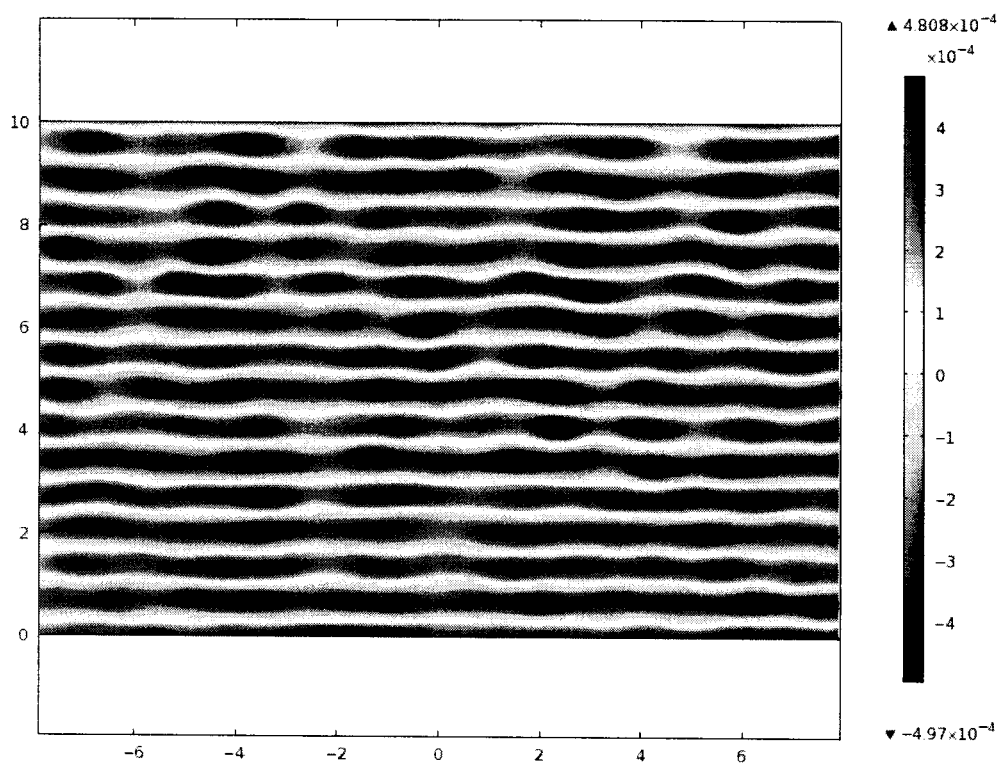
FIG. 7B is an exemplary depiction of the simulated inhomogeneous object of FIG. 6 in which the spatial distribution of the refractive index of the inhomogeneous object is being modified by the ultrasonic plane wave shown modifying the refractive index of the simulated homogeneous object of FIG. 7A.

An exemplary depiction of a simulated homogeneous object in which the spatial distribution of the refractive index of the simulated homogeneous object is being modified by a 1 megahertz, 2 megapascal ultrasonic plane wave (e.g., normal to the object) is depicted in FIG. 7A. Further, an exemplary depiction of the simulated inhomogeneous object of FIG. 6 in which the spatial distribution of the refractive index of the inhomogeneous object is being modified by the 1 megahertz, 2 megapascal ultrasonic plane wave shown modifying the refractive index of the simulated homogeneous object of FIG. 7A is shown in FIG. 7B. In other words, FIG. 7B shows the same ultrasound pattern that is imposed on the homogeneous object of FIG. 7A but imposed on the inhomogeneous object of FIG. 6.

Using the exemplary methods and/or systems described herein, the effects of the 1 megahertz, 2 megapascal ultrasonic plane wave may be removed or subtracted from an obtained image of the simulated inhomogeneous object of FIG. 7B, e.g., in an effort to recreate a final image of the simulated inhomogeneous object of FIG. 6.

Figure 8A:
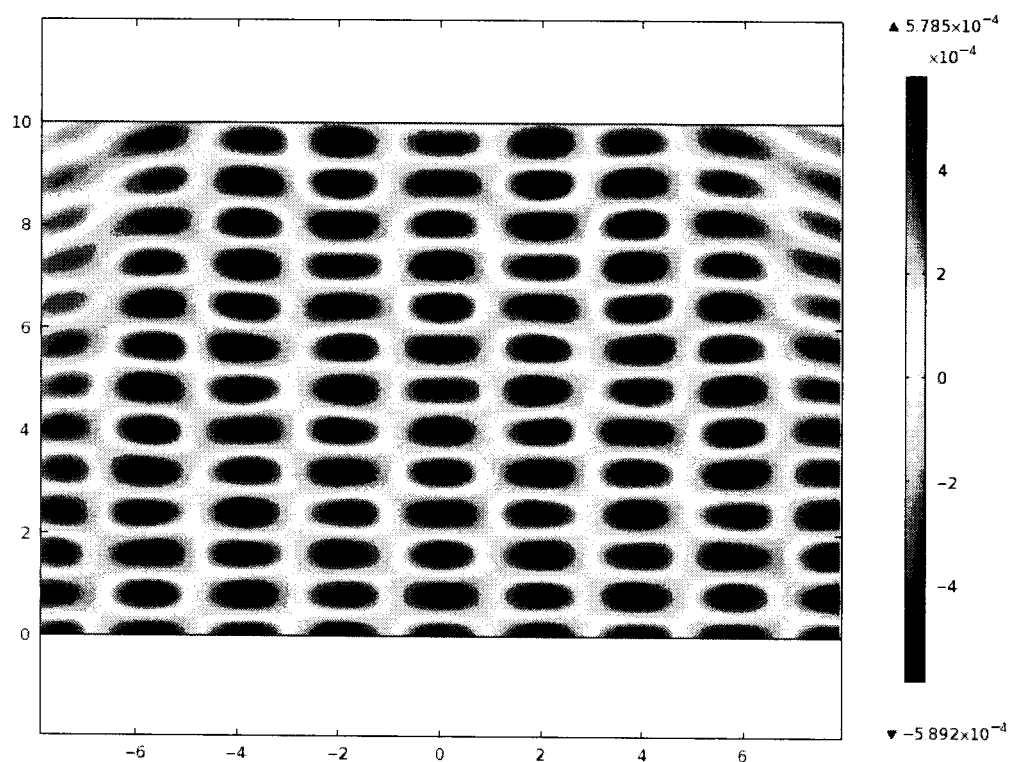
FIG. 8A is an exemplary depiction of a simulated homogeneous object in which the spatial distribution of the refractive index of the homogeneous object is being modified by an ultrasonic standing wave.
Figure 8B:
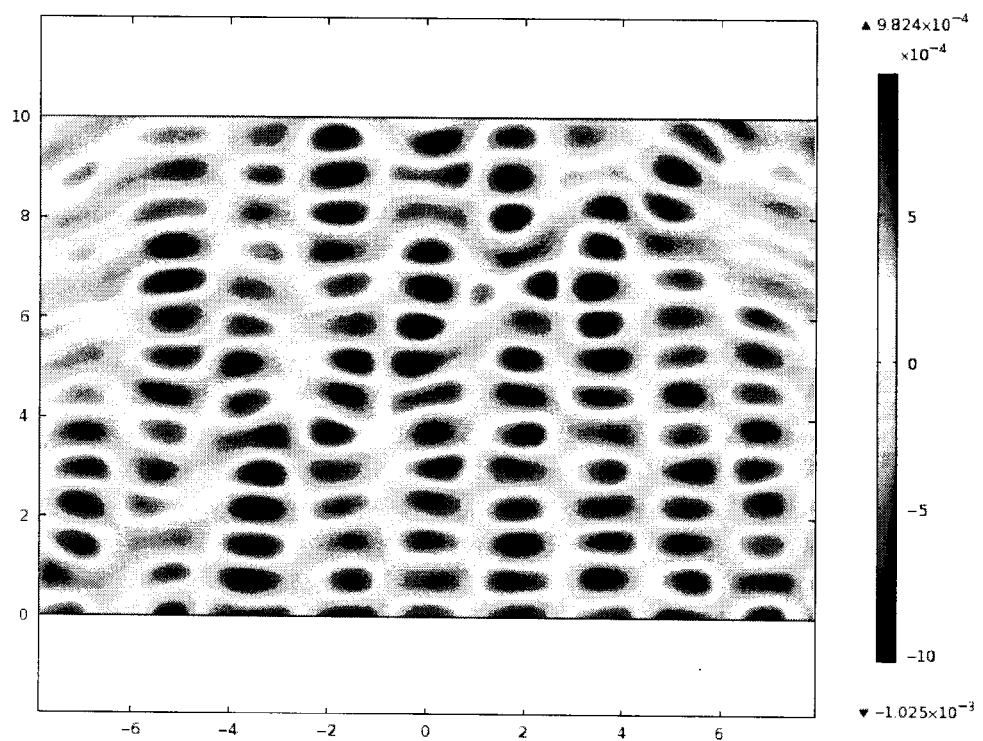
FIG. 8B is an exemplary depiction of the simulated inhomogeneous object of FIG. 6 in which the spatial distribution of the refractive index of the inhomogeneous object is being modified by the ultrasonic standing wave shown modifying the refractive index of the simulated homogeneous object of FIG. 8A.

An exemplary depiction of a simulated homogeneous object in which the spatial distribution of the refractive index of the homogeneous object is being modified by a 1 megahertz, 2 megapascal ultrasonic standing wave (e.g., formed using two beams, one 22.5 degrees from normal and the other −22.5 degrees from normal) is shown in FIG. 8A. Further, an exemplary depiction of the simulated inhomogeneous object of FIG. 6 in which the spatial distribution of the refractive index of the inhomogeneous object is being modified by the 1 megahertz, 2 megapascal ultrasonic standing wave shown modifying the refractive index of the simulated homogeneous object of FIG. 8A is shown in FIG. 8B. In other words, FIG. 8B shows the same ultrasound pattern imposed on the homogeneous object of FIG. 8A but imposed on the inhomogeneous object of FIG. 6.

Using the exemplary methods and/or systems described herein, the effects of the 1 megahertz, 2 megapascal ultrasonic standing wave may be removed or subtracted from an obtained image of the simulated inhomogeneous object of FIG. 8B, e.g., in an effort to recreate a final image of the simulated inhomogeneous object of FIG. 6.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the present disclosure shall not be limiting on the scope of the systems, processes or programs (e.g., the functionality provided by such systems, processes or programs) described herein.

One will recognize that a graphical user interface may be used in conjunction with the embodiments described herein.

The user interface may provide various features allowing for user input thereto, change of input, importation or exportation of files, or any other features that may be generally suitable for use with the processes described herein. For example, the user interface may allow default values to be used or may require entry of certain values, limits, threshold values, or other pertinent information.

Various illustrative embodiments of imaging using OCT are provided in U.S. Pat. No. 7,508,523 B2 entitled "Interferometric System for Complex Image Extraction" issued on Mar. 24, 2009 to Chang et al., which is hereby incorporated by reference. It will be recognized that various other structures and steps described below may be included and/or may be optional. Further, the description herein includes various features of imaging systems and methods. One or more of such features may be used separately or in combination according to the present disclosure.

As described herein, OCT is based on optical interferometry. In the following example, a beamsplitter (e.g., a Michelson interferometer) is used to divide the amplitude of the incident field into a reference arm field and an object arm field (e.g., similar to the imaging set-up configuration 20 depicted in FIG. 3). A mirror reflects the field of the reference arm and the variation of the refractive index of an object at various depths results in a backscattered field. Both reference and backscattered fields interfere at the optical detector. Further, in this example, a complex refractive index is assumed to include both scattering and absorption. Generally, most biological tissues absorb and forward-scatter the incident optical field, and therefore, result in a relatively-weak backscattered field. The addition of the reference field to the weak backscattered field makes the backscattered field easier to measure by the optical detector.

For a coherent optical field normally incident on an object, the optical intensity at the detector may be given by the following (see, e.g., Mickelson, A., *Physical Optics*, 1st ed., Springer (1992)):

$$I(\Delta l, k) \propto \cos(k\Delta l) \tag{1}$$

where $I(\Delta l, k)$ is the intensity at the optical detector, $k = 2\pi/\lambda$ is the wave number, $\lambda$ is the wavelength and $\Delta l$ is the optical pathlength difference between the two interferometer arms. The optical pathlength difference $\Delta l$, due to different depths in the object, produces localized interference fringes at the detector.

On varying the wavelength $\lambda$, equation (1) could be written as $$I(k_i) \propto \cos(k_i \Delta l) \tag{2}$$

where $k_i$ represents the wavenumber for a particular wavelength. In swept-source OCT, the spectrum $\Delta\lambda$ of the incident field is wavelength/frequency swept to obtain different points of the Fourier transform of a depth-scan of the object.

The total field $U^T(r)$ inside and outside of an object may be given by the following:

$$U^T(r) = U^i(r) + U^S(r) \tag{3}$$

where $(r) \equiv (x, y, z)$ is the position vector, $U^i(r)$ is the incident optical field and $U^S(r)$ is the scattered optical field from the object.

The scattered field $U^S(r)$ satisfies the following inhomogeneous Helmholtz equation (see, e.g., Abubakar, A., and van den Berg, P. M., "Iterative forward and inverse algorithms based on domain integral equations for three-dimensional electrical and magnetic objects," Journal of Computational Physics 195(1), 236-262 (2004)):

$$(\nabla^2 + k^2) U^S(r) = -F(r) U^T(r) \tag{4}$$

where $F(r')=k^2 (n^2(r')-1)$ is the scattering potential representing the object and $n(r')$ is the refractive index of an object with volume V.

Using the Green's function technique, equation (4) may be written as an integral equation:

$$U^s(r) = \int_V F(r')U^T(r')G(r-r')d^3r' \quad (5)$$

where $G(r-r')$ is the Green's function.

The Green's function may be given by the following:

$$G(r-r') = \frac{e^{-jk|r-r'|}}{|r-r'|} \quad (6)$$

where $j=\sqrt{-1}$

Using equation (3), the following may be obtained:

$$U^s(r) = \int_V F(r')U^i(r')G(r-r')d^3r' + \int_V F(r')U^s(r')G(r-r')d^3r' \quad (7)$$

Hence, the scattered optical field $U^S(r)$ has two components as shown in the following:

$$U^S(r) = U_{sngl}^S(r) + U_{multi}^S(r) \quad (8)$$

where $U_{sngl}^S(r)$ given by the first term on the right-hand side (RHS) of Equation (7) is the single-scattered light and $U_{multi}^S(r)$ given by the second term of the RHS of Equation (7) is the multiple-scattered light. Further, please note that $U_{sngl}^S(r)$ has a linear relationship with $F(r)$ while $U_{multi}^S(r)$ has a non-linear relationship with $F(r)$.

OCT research often assumes weakly scattering objects, and hence, the first Born approximation, $U^T(r') \approx U^i(r')$ is applied. Thus, any effects of multiple-scattered light may be typically neglected, which is in contradiction to such effects impact on the imaging process.

As described herein, multiple-scattered light may be reduced by modifying optical properties of tissue to be imaged (e.g., modifying the spatial distribution of the tissue's refractive index). Further, as described herein, one exemplary method of modifying optical properties may use ultrasound. The presence of an ultrasound wave in tissue may change the distribution of pressure inside its volume. Further, a change in pressure is associated with a change in tissue density, which may result in a modification of the original distribution of the tissue's refractive index from $n(r)$ to $n(r)+\Delta n(r)$.

Therefore, in the presence of ultrasound, the scattered optical field may be given by the following:

$$U^s(r) = k^2 \int_V \{[n(r')+\Delta n(r')]^2 - 1\}U^i(r')G(r-r')d^3r' + k^2 \int_V \{[n(r')+\Delta n(r')]^2 - 1\}U^s(r')G(r-r')d^3r' \quad (9)$$

Application of an ultrasound wave that results in $\Delta n$ that minimizes the amount of multiple-scattered light (second term of the RHS of Equation (9)) collected at a detector located at position r outside the tissue may be preferred. Since the exact solution of the optimization problem is specific to the unknown $n(r)$, equation (9) may be solved for an assumed tissue configuration, e.g., homogeneous tissue with an appropriate average value of refractive index.

In other words, one or more parameters of ultrasound may be selected so as to provide a known ultrasound pattern, or a known change to the spatial distribution of a homogeneous object's refractive index. The exemplary imaging data processing described herein may use this known ultrasound pattern, or known change to the spatial distribution of a homogenous object's refractive index, to solve for the unknown $n(r)$, thereby obtaining an image of the unmodified object.

Further, the spatial distribution of the refractive index of typical tissue, $n(r)$, may not have a large impact on the scattering of ultrasound in tissue, and as such, in at least one embodiment, it may be assumed that the tissue is homogeneous prior to applying the ultrasound that results in $\Delta n$.

In one or more embodiments, standing-wave ultrasound may be used to create vertical "tunnels" in homogeneous tissue where $\Delta n=0$, surrounded by a traveling wave that may reduce multiple scattered light at the detector, e.g., examples of which may be depicted in, and further described in reference to, FIGS. 8A-8B.

Swept-source OCT systems often ignore the second term in equation (7) (i.e., the multiple-scattered light) and use a Fourier transform (or possibly any other linear de-convolution technique) to obtain the tissue's distribution of the refractive index, $n(r)$. In the present example (e.g., using integrated computational OCT), the second term in equation (9), which represents collected multiple-scattered light, may be minimized, and therefore, the depth of imaging may be increased. A Fourier transform (or possibly any other linear de-convolution technique) may be used to obtain the modified tissue's distribution of the refractive index, $n(r)+\Delta n(r)$.

As described herein, one method of processing imaging data collected when an object is being modified removes or subtracts the modification from the imaging data. For example, after obtaining $n(r)+\Delta n(r)$, $n(r)$ may be obtained by subtracting from it the a priori known $\Delta n$, which, as described herein, may depend on the original spatial distribution of the object's refractive index and the applied ultrasound wave. In at least one embodiment, the known $\Delta n$ may be based on a simulated changed in the spatial distribution of a homogenous object's refractive index.

Further, in at least one embodiment, the $\Delta n(r)$ may be taken into consideration and used during the processing (e.g., linear inversion or non-linear inversion) of the imaging data (e.g., the modification may be taken into consideration and used in the inversion algorithm itself) to obtain or construct a final image.

All patents, patent documents, and references cited herein are incorporated in their entirety as if each were incorporated separately. This disclosure has been provided with reference to illustrative embodiments and is not meant to be construed in a limiting sense.

As described previously, one skilled in the art will recognize that other various illustrative applications may use the techniques as described herein to take advantage of the beneficial characteristics of the methods and systems described herein. Various modifications of the illustrative embodiments, as well as additional embodiments of the disclosure, will be apparent upon reference to this description.

What is claimed:

1. A method for use in imaging an object, wherein the object's refractive index is spatially distributed, wherein the method comprises:

modifying the spatial distribution of the refractive index of the object, wherein modifying the spatial distribution of the refractive index of the object comprises delivering an external stimulus at one or more selected parameters to the object to impose a selected change in the spatial distribution of the refractive index of the object;

imaging the object using interferometry as the spatial distribution of the refractive index of the object is being modified to provide interferometry imaging data;

processing the interferometry imaging data to provide processed imaging data, wherein processing the interferometry imaging data to provide processed imaging data comprises:

providing the one or more selected parameters of the external stimulus, and processing the interferometry imaging data with one or more image processing algorithms that take into account the selected change in the spatial distribution of the refractive index of the object by using the one or more selected parameters of the external stimulus when processing the interferometry imaging data to provide the processed imaging data, wherein processing the interferometry imaging data to provide processed imaging data comprises inverting the interferometry imaging data based in part on the modification to the spatial distribution of the refractive index of the object; and constructing an image of the object based on the processed imaging data.

2. The method of claim 1, wherein the external stimulus comprises ultrasound, and wherein modifying the spatial distribution of the refractive index of the object comprises delivering ultrasound to the object to modify the spatial distribution of the refractive index of the object to reduce multiple-scattered light.

3. The method of claim 2, wherein delivering ultrasound to the object to modify the spatial distribution of the refractive index of the object comprises delivering ultrasound to the object at the one or more selected parameters to impose the selected change in the spatial distribution of the refractive index of the object.

4. The method of claim 3, wherein delivering ultrasound to the object at the one or more selected parameters comprises delivering a first 1 megahertz, 2 megapascal ultrasound beam at 22.5 degrees from normal to the object and a second 1 megahertz, 2 megapascal ultrasound beam at negative 22.5 degrees from normal to the object to impose a standing wave in the spatial distribution of the refractive index of the object.

5. The method of claim 1, wherein modifying the spatial distribution of the refractive index of the object and imaging the object comprises modifying the spatial distribution of the refractive index of the object in a known relationship to the imaging of the object using interferometry.

6. The method of claim 1, wherein modifying the spatial distribution of the refractive index of the object comprises modifying a spatial distribution of pressure of the object.

7. The method of claim 1, wherein imaging the object using interferometry comprises imaging the object using optical coherence tomography.

8. The method of claim 1, wherein imaging the object using interferometry comprises delivering electromagnetic energy to the object using a swept-source.

9. The method of claim 1, wherein processing the interferometry imaging data to provide processed imaging data comprises removing effects of the modification to the spatial distribution of the refractive index of the object from the interferometry imaging data.

10. A system for use in imaging an object, wherein the object's refractive index is spatially distributed, wherein the system comprises:

modification apparatus comprising at least one of an ultrasound transducer, a heater, and a pressure applicator, wherein the modification apparatus is configured to modify the spatial distribution of the refractive index of an object at one or more selected parameters, wherein the modification apparatus delivers an external stimulus at the one or more selected parameters to the object to impose a selected change in the spatial distribution of the refractive index of the object;

interferometry apparatus configured to image the object to provide interferometry imaging data as the spatial distribution of the refractive index of the object is being modified using the modification apparatus; and processing apparatus configured to:

receive the imaging data from the interferometry apparatus, provide the one or more selected parameters of the external stimulus, process the interferometry imaging data with one or more image processing algorithms that take into account the selected change in the spatial distribution of the refractive index of the object by using the one or more selected parameters of the external stimulus when processing the interferometry imaging data to provide the processed imaging data, and construct an image of the object based on the processed imaging data, wherein, to process the interferometry imaging data with one or more image processing algorithms, the processing apparatus is further configured to invert the imaging data based in part on the modification to the spatial distribution of the refractive index of the object.

11. The system of claim 10, wherein the external stimulus comprises ultrasound, and wherein the modification apparatus comprises an ultrasound transducer configured to deliver ultrasound to the object to modify the spatial distribution of the refractive index of the object to reduce multiple-scattered light.

12. The system of claim 11, wherein the ultrasound transducer is further configured to deliver ultrasound to the object at the one or more selected parameters to impose the selected change in the spatial distribution of the refractive index of the object.

13. The system of claim 12, wherein the ultrasound transducer is further configured to deliver a first 1 megahertz, 2 megapascal ultrasound beam at 22.5 degrees from normal to the object and a second 1 megahertz, 2 megapascal ultrasound beam at negative 22.5 degrees from normal to the object to impose a standing wave in the spatial distribution of the refractive index of the object.

14. The system of claim 10, wherein the modification apparatus is operably coupled to the interferometry apparatus such that the relationship between the modification to the spatial distribution of the refractive index of the object and an imaging volume of the object to be imaged by the interferometer apparatus is known.

15. The system of claim 10, wherein the modification apparatus is further configured to modify a spatial distribution of pressure of the object.

16. The system of claim 10, wherein the interferometry apparatus comprises optical coherence tomography apparatus configured to image the object using optical coherence tomography.

17. The system of claim 10, wherein the interferometry apparatus comprises a swept-source to deliver electromagnetic energy to the object for use in imaging the object.

18. The system of claim 10, wherein, to process the interferometry imaging data with one or more image processing algorithms, the processing apparatus is further configured to remove effects of the modification to the spatial distribution of the refractive index of the object from the imaging data.

19. A method for use in imaging an object, wherein the object's refractive index is spatially distributed, wherein the method comprises:
modifying the spatial distribution of the refractive index of the object, wherein modifying the spatial distribution of the refractive index of the object comprises delivering an external stimulus at one or more selected parameters to the object to impose a selected change in the spatial distribution of the refractive index of the object;
imaging the object using interferometry as the spatial distribution of the refractive index of the object is being modified to provide interferometry imaging data;
processing the interferometry imaging data to provide processed imaging data, wherein processing the interferometry imaging data to provide processed imaging data comprises:
providing the one or more selected parameters of the external stimulus, and
processing the interferometry imaging data with one or more image processing algorithms that take into account the selected change in the spatial distribution of the refractive index of the object by using the one or more selected parameters of the external stimulus when processing the interferometry imaging data to provide the processed imaging data, wherein processing the interferometry imaging data to provide processed imaging data comprises removing effects of the modification to the spatial distribution of the refractive index of the object from the interferometry imaging data; and
constructing an image of the object based on the processed imaging data.

20. The method of claim 19, wherein the external stimulus comprises ultrasound, and wherein modifying the spatial distribution of the refractive index of the object comprises delivering ultrasound to the object to modify the spatial distribution of the refractive index of the object to reduce multiple-scattered light.

21. The method of claim 20, wherein delivering ultrasound to the object to modify the spatial distribution of the refractive index of the object comprises delivering ultrasound to the object at the one or more selected parameters to impose the selected change in the spatial distribution of the refractive index of the object.

22. The method of claim 21, wherein delivering ultrasound to the object at the one or more selected parameters comprises delivering a first 1 megahertz, 2 megapascal ultrasound beam at 22.5 degrees from normal to the object and a second 1 megahertz, 2 megapascal ultrasound beam at negative 22.5 degrees from normal to the object to impose a standing wave in the spatial distribution of the refractive index of the object.

23. The method of claim 19, wherein modifying the spatial distribution of the refractive index of the object and imaging the object comprises modifying the spatial distribution of the refractive index of the object in a known relationship to the imaging of the object using interferometry.

24. The method of claim 19, wherein modifying the spatial distribution of the refractive index of the object comprises modifying a spatial distribution of pressure of the object.

25. The method of claim 19, wherein imaging the object using interferometry comprises imaging the object using optical coherence tomography.

26. The method of claim 19, wherein imaging the object using interferometry comprises delivering electromagnetic energy to the object using a swept-source.

27. The method of claim 19, wherein processing the interferometry imaging data to provide processed imaging data comprises inverting the interferometry imaging data based in part on the modification to the spatial distribution of the refractive index of the object.

28. A system for use in imaging an object, wherein the object's refractive index is spatially distributed, wherein the system comprises:
modification apparatus comprising at least one of an ultrasound transducer, a heater, and a pressure applicator, wherein the modification apparatus is configured to modify the spatial distribution of the refractive index of an object at one or more selected parameters, wherein the modification apparatus delivers an external stimulus at the one or more selected parameters to the object to impose a selected change in the spatial distribution of the refractive index of the object;
interferometry apparatus configured to image the object to provide interferometry imaging data as the spatial distribution of the refractive index of the object is being modified using the modification apparatus; and
processing apparatus configured to:
receive the imaging data from the interferometry apparatus,
provide the one or more selected parameters of the external stimulus,
process the interferometry imaging data with one or more image processing algorithms that take into account the selected change in the spatial distribution of the refractive index of the object by using the one or more selected parameters of the external stimulus when processing the interferometry imaging data to provide the processed imaging data, and construct an image of the object based on the processed imaging data,
wherein, to process the interferometry imaging data with one or more image processing algorithms, the processing apparatus is further configured to remove effects of the modification to the spatial distribution of the refractive index of the object from the imaging data.

29. The system of claim 28, wherein the external stimulus comprises ultrasound, and wherein the modification apparatus comprises an ultrasound transducer configured to deliver ultrasound to the object to modify the spatial distribution of the refractive index of the object to reduce multiple-scattered light.

30. The system of claim 29, wherein the ultrasound transducer is further configured to deliver ultrasound to the object at the one or more selected parameters to impose the selected change in the spatial distribution of the refractive index of the object.

31. The system of claim 30, wherein the ultrasound transducer is further configured to deliver a first 1 megahertz, 2 megapascal ultrasound beam at 22.5 degrees from normal to the object and a second 1 megahertz, 2 megapascal ultrasound beam at negative 22.5 degrees from normal to the object to impose a standing wave in the spatial distribution of the refractive index of the object.

32. The system of claim 28, wherein the modification apparatus is operably coupled to the interferometry apparatus such that the relationship between the modification to the spatial distribution of the refractive index of the object and an imaging volume of the object to be imaged by the interferometer apparatus is known.

33. The system of claim 28, wherein the modification apparatus is further configured to modify a spatial distribution of pressure of the object.

34. The system of claim 28, wherein the interferometry apparatus comprises optical coherence tomography apparatus configured to image the object using optical coherence tomography.

35. The system of claim 28, wherein the interferometry apparatus comprises a swept-source to deliver electromagnetic energy to the object for use in imaging the object.

36. The system of claim 28, wherein, to process the interferometry imaging data with one or more image processing algorithms, the processing apparatus is further configured to invert the imaging data based in part on the modification to the spatial distribution of the refractive index of the object.

* * * * *